US010098570B2

(12) United States Patent
Poore et al.

(10) Patent No.: US 10,098,570 B2
(45) Date of Patent: Oct. 16, 2018

(54) PORTABLE SPIROMETER AND METHOD FOR MONITORING LUNG FUNCTION

(71) Applicant: VIGOR MEDICAL SYSTEMS, INC., Durham, NC (US)

(72) Inventors: Gregory Poore, La Jolla, CA (US); Daniel Chander, Villa Martia (SG); Melody Xuan Lim, Chicago, IL (US)

(73) Assignee: VIGOR MEDICAL SYSTEMS, INC., Durham, NC (US)

( * ) Notice: Subject to any disclaimer, the term of this patent is extended or adjusted under 35 U.S.C. 154(b) by 0 days.

(21) Appl. No.: 15/696,780

(22) Filed: Sep. 6, 2017

(65) Prior Publication Data

US 2018/0064367 A1     Mar. 8, 2018

Related U.S. Application Data

(60) Provisional application No. 62/554,266, filed on Sep. 5, 2017, provisional application No. 62/534,462, filed (Continued)

(51) Int. Cl.
*A61B 5/087* (2006.01)
*A61B 5/097* (2006.01)
(Continued)

(52) U.S. Cl.
CPC ............ *A61B 5/087* (2013.01); *A61B 5/0004* (2013.01); *A61B 5/0022* (2013.01); *A61B 5/097* (2013.01);
(Continued)

(58) Field of Classification Search
CPC ..... A61B 5/087; A61B 5/0004; A61B 5/0022; A61B 5/097; A61B 5/4848; A61B 5/6898;
(Continued)

(56) References Cited

U.S. PATENT DOCUMENTS 3,735,752 A     5/1973   Rodder et al.
4,736,750 A     4/1988   Valdespino et al.
(Continued)

FOREIGN PATENT DOCUMENTS

CN     2367251 Y     3/2000
CN     2436100 Y     6/2001
(Continued)

OTHER PUBLICATIONS

Vigor Medical Systems, Inc., International Patent Application No. PCT/US2017/050239, International Search Report and Written Opinion, dated Dec. 15, 2017.

*Primary Examiner* — Navin Natnithithadha
(74) *Attorney, Agent, or Firm* — Michael G. Johnston; Moore & Van Allen PLLC

(57) ABSTRACT

A spirometer comprises a housing defining a fluid flow pathway extending between a first end and a second end, a first opening along the pathway and a second opening longitudinally spaced along the pathway from the first opening. A flow chamber defining a fluid flow pathway is disposed within the housing between the first opening and the second opening, the flow chamber including an elongated resistive element along the central longitudinal axis of the flow chamber for defining a flow passage through the flow chamber between the resistive element and the inner surface of the flow chamber. The flow chamber conditions fluid flow for accurate sensing of the fluid flow over a range. A pressure sensor is disposed within the housing in fluid communication with the first opening and the second opening for sensing a pressure differential between the first opening and the second opening and producing an electric signal that corresponds with the rate of fluid flow through the housing. The described spirometer and associated software has a variety of applications in the evaluation, diagnosis, (Continued)

monitoring, and improvement of respiratory conditions as well as digitally-delivered respiratory rehabilitation programs and clinical trials.

22 Claims, 21 Drawing Sheets

Related U.S. Application Data on Jul. 19, 2017, provisional application No. 62/533,368, filed on Jul. 17, 2017, provisional application No. 62/533,361, filed on Jul. 17, 2017, provisional application No. 62/383,893, filed on Sep. 6, 2016.

(51) Int. Cl.
  G01F 1/34 (2006.01)
  A61B 5/00 (2006.01)
(52) U.S. Cl.
  CPC ......... A61B 5/4848 (2013.01); A61B 5/6898 (2013.01); A61B 5/7267 (2013.01); A61B 5/7282 (2013.01); A61B 5/744 (2013.01); A61B 5/7465 (2013.01); A61B 2560/045 (2013.01); A61B 2560/0431 (2013.01); A61B 2562/0247 (2013.01); G01F 1/34 (2013.01)
(58) Field of Classification Search
  CPC ..... A61B 5/7267; A61B 5/7282; A61B 5/744; A61B 5/7465; A61B 2560/0431; A61B 2560/045; A61B 2562/0247; G01F 1/34
  USPC .................................................. 600/529–538
  See application file for complete search history.

(56) References Cited

U.S. PATENT DOCUMENTS

| | | | |
|---|---|---|---|
| 5,722,417 A | 3/1998 | Garbe | |
| 5,750,982 A | 5/1998 | Dokyi | |
| 6,203,502 B1* | 3/2001 | Hilgendorf | A61B 5/087 128/200.11 |
| 6,435,183 B1* | 8/2002 | Farman | A61M 16/00 128/204.25 |
| 6,585,662 B1* | 7/2003 | Jones | A61B 5/087 600/529 |
| 6,681,643 B2* | 1/2004 | Heinonen | G01F 1/36 600/538 |
| 6,699,188 B2 | 3/2004 | Wessel | |
| 6,915,705 B1* | 7/2005 | Truitt | A61B 5/087 73/861.52 |
| 7,063,669 B2 | 6/2006 | Brawner et al. | |
| 7,172,557 B1 | 2/2007 | Parker | |
| 7,584,108 B2 | 9/2009 | Brown | |
| 8,034,002 B2 | 10/2011 | Coifman | |
| 8,092,224 B2 | 1/2012 | Walker et al. | |
| 8,353,844 B2* | 1/2013 | Jin | A61B 5/091 600/529 |
| 8,449,474 B2* | 5/2013 | Schuessler | A61B 5/085 417/415 |
| 8,583,459 B2 | 11/2013 | Neben et al. | |
| 9,113,818 B2* | 8/2015 | Brunner | A61B 5/0876 |
| 9,138,167 B1 | 9/2015 | Leydon | |
| 9,207,715 B2 | 12/2015 | Filipovic et al. | |
| 9,286,615 B2 | 3/2016 | Hyde et al. | |
| 9,443,061 B2 | 9/2016 | Hyde et al. | |
| 2002/0116994 A1* | 8/2002 | Heinonen | G01F 1/36 73/196 |
| 2003/0120169 A1* | 6/2003 | Jones | A61B 5/087 600/538 |
| 2006/0036134 A1 | 2/2006 | Tarassenko et al. | |
| 2006/0218011 A1 | 9/2006 | Walker et al. | |
| 2008/0177574 A1 | 7/2008 | Lara Gonzalez et al. | |
| 2009/0020120 A1* | 1/2009 | Schatzl | A61B 5/087 128/204.22 |
| 2009/0253994 A1* | 10/2009 | Schuessler | A61B 5/085 600/538 |
| 2011/0119075 A1 | 5/2011 | Dhoble | |
| 2011/0119076 A1 | 5/2011 | Dhoble | |
| 2011/0119290 A1 | 5/2011 | Dhoble | |
| 2011/0125517 A1 | 5/2011 | Dhoble | |
| 2011/0125518 A1 | 5/2011 | Dhoble | |
| 2011/0125519 A1 | 5/2011 | Dhoble | |
| 2011/0125520 A1 | 5/2011 | Dhoble | |
| 2011/0125521 A1 | 5/2011 | Dhoble | |
| 2011/0306859 A1 | 12/2011 | Saldivar et al. | |
| 2012/0130265 A1 | 5/2012 | Cha et al. | |
| 2012/0136271 A1 | 5/2012 | Shavit | |
| 2012/0302910 A1* | 11/2012 | Freeman | A61M 16/021 600/538 |
| 2013/0018240 A1 | 1/2013 | McCoy | |
| 2013/0053719 A1 | 2/2013 | Wekell | |
| 2013/0144655 A1 | 6/2013 | Neben et al. | |
| 2013/0190641 A1 | 7/2013 | Gonnen et al. | |
| 2013/0317379 A1 | 11/2013 | Brimer et al. | |
| 2014/0066731 A1 | 3/2014 | Sadasivam | |
| 2014/0073969 A1 | 3/2014 | Lou et al. | |
| 2014/0081087 A1 | 3/2014 | Yu | |
| 2014/0142456 A1 | 5/2014 | Fischer et al. | |
| 2014/0206949 A1 | 7/2014 | Lucas | |
| 2015/0126888 A1 | 5/2015 | Patel et al. | |
| 2015/0126889 A1 | 5/2015 | Frey et al. | |
| 2015/0148634 A1* | 5/2015 | Garudadri | A61B 5/02141 600/323 |
| 2015/0150483 A1 | 6/2015 | Mangell | |
| 2015/0150484 A1 | 6/2015 | Wekell | |
| 2015/0157230 A1 | 6/2015 | Tseng et al. | |
| 2015/0164373 A1* | 6/2015 | Davis | A61B 5/082 600/532 |
| 2015/0320949 A1* | 11/2015 | Jaffe | A61B 5/087 600/538 |
| 2015/0359489 A1 | 12/2015 | Baudenbacher et al. | |
| 2016/0015324 A1 | 1/2016 | Du Bois | |
| 2016/0015328 A1 | 1/2016 | Dahlberg et al. | |
| 2016/0055415 A1 | 2/2016 | Baxi | |
| 2016/0106342 A1 | 4/2016 | Razavi et al. | |
| 2016/0106627 A1 | 4/2016 | Geman et al. | |
| 2016/0136366 A1 | 5/2016 | Bennett | |
| 2016/0150995 A1 | 6/2016 | Ratto et al. | |
| 2016/0242701 A1 | 8/2016 | Gonnen et al. | |
| 2016/0287139 A1* | 10/2016 | Luttrell | G07F 17/3244 |
| 2017/0266399 A1* | 9/2017 | Campana | A61M 16/0003 |

FOREIGN PATENT DOCUMENTS

| | | |
|---|---|---|
| DE | 102005026933 A1 | 12/2006 |
| DE | 102005026933 B4 | 9/2010 |
| EP | 3050513 A1 | 8/2016 |
| ES | 2188405 A1 | 6/2003 |
| ES | 2188405 B1 | 2/2005 |
| JP | 5751509 U | 3/1982 |
| KR | 100760065 B1 | 9/2007 |
| WO | 2004082161 A1 | 9/2004 |
| WO | 2013088351 A1 | 6/2013 |
| WO | 2015066562 A2 | 5/2015 |
| WO | 2015117046 A1 | 8/2015 |
| WO | 2015145424 A1 | 10/2015 |
| WO | 2016161036 A1 | 10/2016 |

* cited by examiner

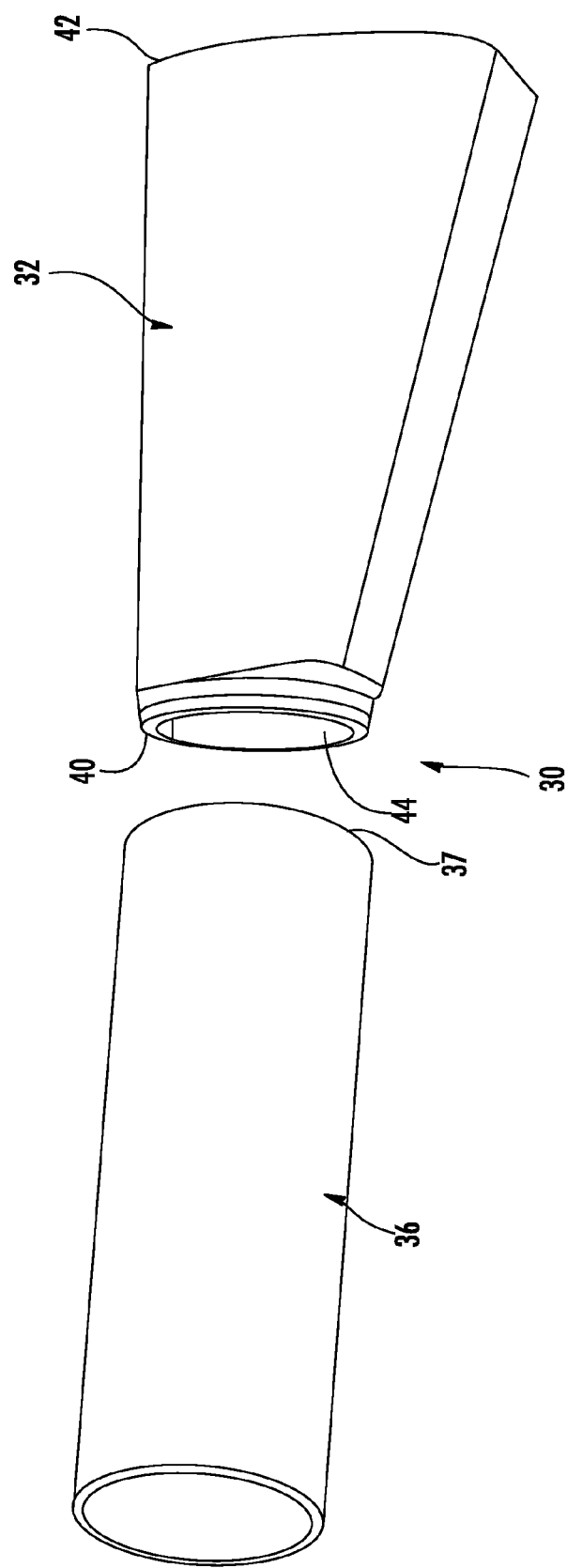

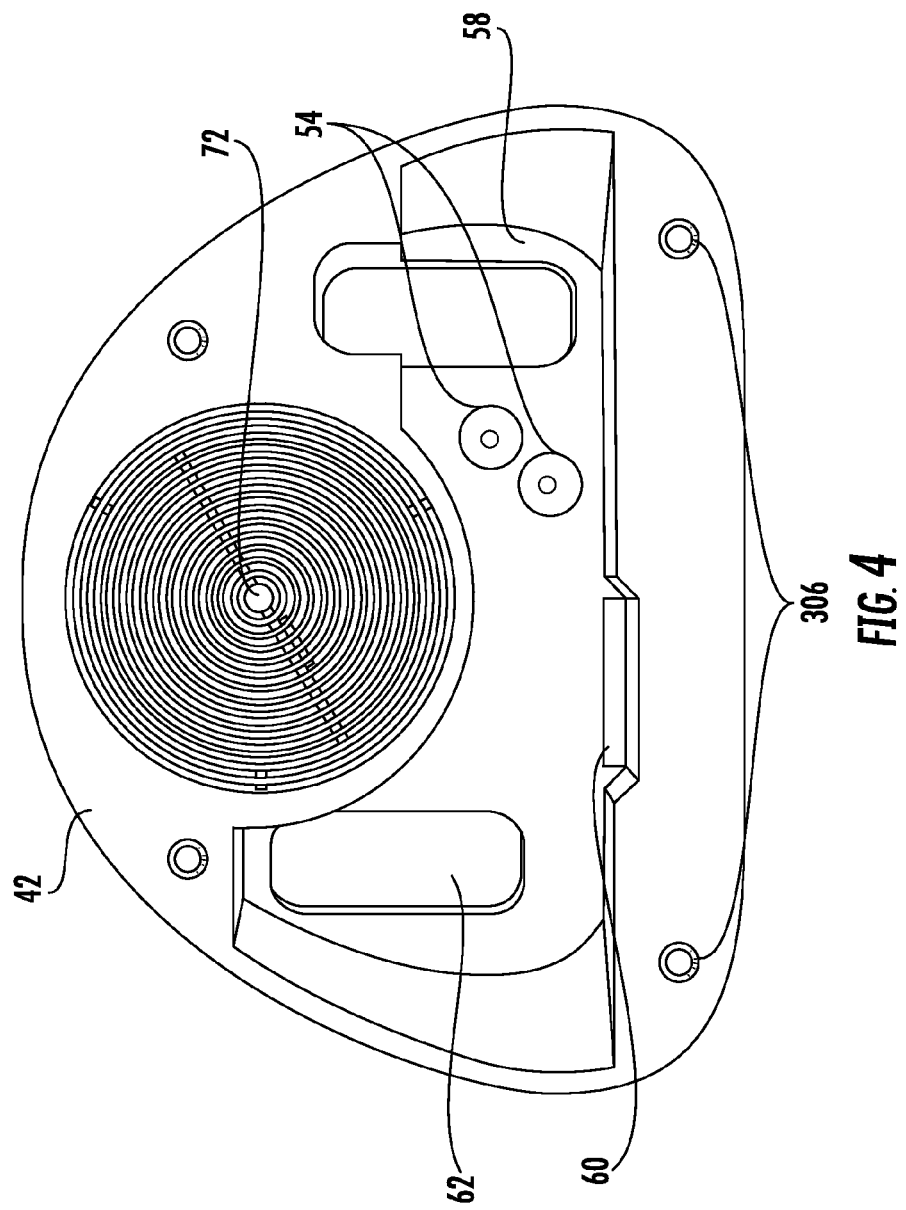

PORTABLE SPIROMETER AND METHOD FOR MONITORING LUNG FUNCTION

CROSS-REFERENCES

This application is related to U.S. provisional application No. 62/383,893, filed Sep. 6, 2016, U.S. provisional application No. 62/533,361, filed Jul. 17, 2017, U.S. provisional application No. 62/533,368, filed Jul. 17, 2017, U.S. provisional application No. 62/534,462, filed Jul. 19, 2017, and U.S. provisional application No. 62/554,266, filed Sep. 5, 2017. The contents of the provisional applications are incorporated herein by reference in their entirety, and the benefit of the filing dates of the provisional applications are hereby claimed for all purposes that are legally served by such claim for the benefit of the filing dates.

BACKGROUND

A spirometer is described and, more particularly, a portable spirometer having multiple concentric air flow tubes for use in detecting and diagnosing pulmonary disorders and including a wireless connection to a mobile device for transferring data to other computers for remote monitoring patient lung function and performance.

A spirometer is a device that monitors respiration by measuring the amount of air inhaled and exhaled by a patient for a period of time. Many conventional spirometers evaluate air flow by measuring the pressure difference across an obstruction placed in the flow channel at an intermediate portion of the spirometer. A differential pressure sensor is connected to two outlets from the flow channel on either side of the flow obstruction. The obstruction can be comprised by a variety of means including a restriction in the flow channel or a fine wire mesh or ceramic screen. The sensor signal as a differential pressure is then converted into a voltage as electronic data, which can be displayed on a monitor, transmitted to a computer, or shared with others.

Spirometers are used for the diagnosis of pulmonary diseases. Spirometers are also used as a part of pulmonary function testing and to evaluate lung function in people with obstructive or restrictive lung disease, such as asthma, emphysema, chronic obstructive pulmonary disease (COPD) or other airway disorders or conditions relating to the respiratory system. For example, asthma can cause chronic or acute symptoms that can range from annoying to life threatening. These symptoms typically range from coughing, wheezing, and shortness of breath to drastically decreased air exchange as measured by a spirometer.

Determining lung function uses various types of spirometric examinations in which the vital capacity and forced expiratory volume at predetermined intervals are measured for comparison with expected values. Evaluation of lung function is through comparison of the subject's vital capacity with theoretical values which are dictated by the sex, age and height of the subject. A number of criteria are used for determining the condition of the patient. Two often used criteria are forced vital capacity (FVC) of the patient's lungs and the forced expiratory volume timed for one second ($FEV_1$). The ratio of these two volumes ($FEV_1/FVC$) is also used for diagnostic purposes. In normal patients the ratio of $FEV_1/FVC$ is greater than 75% (0.75). A ratio of less than 75% is indicative of an obstructive impairment, such as asthma or emphysema.

Spirometers can also measure key parameters that are precursor symptoms of asthma, such as peak respiratory flow or peak expiratory flow (PEF), which is defined as the maximum flow rate recorded during a forced expiration of air from the lungs. Respiratory conditions can be monitored by measuring peak flow with a portable spirometer. Peak expiratory airflow, as well as other lung function measurements, can be used to identify problems before they become apparent to the patient. With careful monitoring of these values, it may be possible to help the patient recognize impending problems and avert an emergency or lessen its severity.

Spirometers are also used to study the progress of lung performance to assist in the treatment of a variety of airway disorders, diseases and conditions. Remotely monitoring a treatment plan put in place with a healthcare provider helps maintain adherence to the treatment plan by the patient and can additionally include tracking medication usage for review by the healthcare provider. For example, pulmonologists overseeing asthma patients recommend that patients with moderate to severe asthma should record their peak expiratory flow on a daily basis to determine the effectiveness of the treatment given to them. It is also important to know whether a patient is administering medication according to the treatment plan. Therefore, a need exists for methods and systems that track a patient's physiological parameters (e.g., peak expiratory airflow in asthma, FEV1 in COPD, FVC in IPF, etc.) and medication administration on a continual basis, rather than be limited to periodic visits by the patient to their healthcare provider to help manage their respiratory diseases acutely and/or chronically.

Conventional spirometers also have some disadvantages, including an inability of some designs to equally and accurately measure flow across the full dynamic range of flow rates or to laminarize high flow rates well. Moreover, designs that approach this linear transduction are often plagued by high cost or physically large size, precluding the opportunity for individuals to purchase or carry them around for use when they may be most needed. From a human factors standpoint, other device designs suffer from the inclusion of moving parts or poorly accessible parts that can impact cleaning, device sanitation, and ultimately reduce measurement accuracy from wear-and-tear and clogging. Additionally, many of these conventional desktop spirometers cannot be converted to smaller form factors because of induced turbulence caused by passing very high flow rates (up to 840 liters/minute) through narrow passageways that comply with average mouth sizes (scale of centimeters). Mathematically, this turbulence can be modeled by the Reynolds number of the fluid, which will exceed a critical level under conditions of high volumetric flow rate, large hydraulic diameter, and small cross-section area, resulting in a fluid flow that has eddies and non-uniform flow distributions. In turbulent flow, local velocities and pressures of fluid fluctuate irregularly and in a random manner, which can create deviance in the flow rate measurement that only grows during volumetric integration, eventually approaching or exceeding allowable error.

For the foregoing reasons, there is a need for a portable, low-cost, durable spirometer and method that provides reliable results via laminarization of flow across a wide dynamic range of flow rates for measuring and monitoring lung function. In some cases, such a device could tremendously benefit patient health for chronic lung conditions such as asthma, COPD, cystic fibrosis, IPF, and so forth; in other cases, such a device could be used to digitally deliver remote pulmonary rehabilitation trials that have been traditionally performed in cardiopulmonary rehabilitation centers or hospitals; in still other cases; such a device could enable new forms of digital clinical trials that track and aggregate granular lung function data for phase I through phase IV trials. Thus, such a spirometer should be sufficiently easy to use for individuals themselves to perform remote monitoring of their lung function. The spirometer should also be capable of interfacing with a mobile device or a desktop computer or the internet to allow convenient data collection and transfer so that healthcare professionals, clinical trial coordinators, and any other privileged individual can check the reliability of the results and implementation and monitoring of a treatment plan, study protocol, rehabilitation plan, and so forth.

SUMMARY

A spirometer is provided for sensing fluid flow from a patient breathing through the spirometer. The spirometer comprises a tubular housing having an open first end and an open second end. The housing defines a fluid flow pathway extending between the first end and the second end, a first opening along the pathway and through which fluid flow enters, and a second opening longitudinally spaced along the pathway from the first opening and through which fluid flow enters. A flow chamber defines a fluid flow pathway and is disposed within the housing between the first opening and the second opening. The flow chamber includes an elongated resistive element along the central longitudinal axis of the flow chamber for defining a flow passage through the flow chamber between the resistive element and the inner surface of the flow chamber. The flow chamber conditions fluid flow for accurate sensing of the flow over a range of fluid flow through the housing. A pressure sensor is disposed within the housing. The pressure sensor is in fluid communication with the first opening and the second opening for sensing a pressure differential between the first opening and the second opening and producing an electric signal in response to fluid flow through the housing. The electric signal has a magnitude that corresponds with the rate of fluid flow through the housing and a sign that corresponds with the directionality of fluid flow through the housing.

In one aspect, the flow chamber and pressure sensing elements have no moving parts. Fluid flow through the flow chamber is substantially parallel to the longitudinal axis of the flow chamber, which has a cylindrical cross-section.

In another aspect, the flow chamber further comprises at least one elongated tubular element disposed between the resistive element and the inner surface of the flow chamber element for defining a plurality of flow passages through the flow chamber. The flow chamber is configured to laminarize the fluid flow. The elongated resistive element may be removable from the rest of the device.

In yet another aspect, the pressure sensor is a transducer, and may be a self-calibrating transducer. The pressure sensor is configured to be connected to a display device or mobile computing device.

In a further aspect, the spirometer is configured to be connected to the display device or mobile computing device by a physical connection. The spirometer may further comprise a radio frequency transmitter (RF) configured to be connected to a display device or mobile computing device by a wireless connection.

In another aspect, the display device or mobile computing device is a smartphone, a personal computer, or a remote server.

In still another aspect, the spirometer may further comprise a mouth piece configured to be attached to the first end of the housing, the mouth piece having an opening through the mouth piece for transmitting human breath. The mouth piece may be releasably attached to the housing for changing the mouth piece for use with different patients.

In another embodiment, a lung function testing system for a patient comprises a spirometer for sensing fluid flow from the patient breathing through the spirometer. The spirometer comprises a tubular housing having an open first end and an open second end. The housing defines a fluid flow pathway extending between the first end and the second end, a first opening along the pathway and through which fluid flow enters, and a second opening longitudinally spaced along the pathway from the first opening and through which fluid flow enters. A flow chamber defining a fluid flow pathway is disposed within the housing between the first opening and the second opening. The flow chamber includes an elongated resistive element along the central longitudinal axis of the flow chamber for defining a flow passage through the flow chamber between the resistive element and the inner surface of the flow chamber. The flow chamber conditions the fluid flow for accurate sensing of the flow over a range of fluid flow through the housing. A pressure sensor is disposed within the housing. The pressure sensor is in fluid communication with the first opening and the second opening for sensing a pressure differential between the first opening and the second opening and producing an electric signal in response to fluid flow through the housing. The electric signal has a magnitude that corresponds with the rate of fluid flow through the housing and a sign that corresponds with the directionality of fluid flow through the housing. A microprocessor is coupled to the pressure sensor for data acquisition and processing the electrical signal to evaluate lung function according to the fluid flow rate through the housing.

In one aspect, the lung function testing system may further comprise a transmitter, and an external device comprising a display device or mobile computing device for monitoring the individual, wherein the spirometer and the external device are each connected by at least one network, the spirometer being operable to collect at least one fluid flow measurement of the individual and transmit the at least one fluid flow measurement to the at least one network.

In another embodiment, a method of evaluating respiratory fluid flow of a patient is provided. The respiratory fluid flow evaluation method comprises the steps of providing a spirometer for sensing fluid flow from the patient breathing through the spirometer. The spirometer comprises a tubular housing having an open first end and an open second end. The housing defines a fluid flow pathway extending between the first end and the second end, a first opening along the pathway and through which fluid flow enters, and a second opening longitudinally spaced along the pathway from the first opening and through which fluid flow enters. A flow chamber defining a fluid flow pathway is disposed within the housing between the first opening and the second opening. The flow chamber includes an elongated resistive element along the central longitudinal axis of the flow chamber for defining a flow passage through the flow chamber between the resistive element and the inner surface of the flow chamber. The flow chamber conditions the fluid flow for accurate sensing of the flow over a range of fluid flow through the housing. A pressure sensor disposed within the housing is in fluid communication with the first opening and the second opening for sensing a pressure differential between the first opening and the second opening and producing an electric signal in response to fluid flow through the housing. The electric signal has a magnitude that corresponds with the rate of fluid flow through the housing and a sign that corresponds with the directionality of fluid flow through the housing. The method further comprises the steps of breathing into the spirometer by exhaling or inhaling a flowing fluid through the spirometer from the first end to exit the second end, sensing flowing fluid within the spirometer to provide flow data according to the fluid flow; and evaluating lung function according to the flow data. The software coupled to the described embodiment walks the patient through the process of performing a procedurally correct test.

In one aspect, the respiratory fluid flow evaluation method further comprises the step of providing fluid flow measurement data to at least one of a support network computing device and a healthcare provider computing device.

In another aspect, the respiratory fluid flow evaluation method further comprises the step of providing fluid flow measurement data to a healthcare provider computing device.

In yet another aspect, the software linked to the support network computing device or the healthcare provider computing device employs any variety or set of learning algorithms to automatically diagnose an individual's respiratory condition based on the flow data or any other user-specific health information in combination with the flow data.

In another embodiment, a system is provided for remotely delivering the contents of a pulmonary treatment or rehabilitation program to an individual. The digital treatment or rehabilitation program system comprises providing a spirometer for sensing fluid flow from the individual breathing through the spirometer. The spirometer comprises a tubular housing having an open first end and an open second end. The housing defines a fluid flow pathway extending between the first end and the second end, a first opening along the pathway and through which fluid flow enters, and a second opening longitudinally spaced along the pathway from the first opening and through which fluid flow enters. A flow chamber defining a fluid flow pathway is disposed within the housing between the first opening and the second opening. The flow chamber includes an elongated resistive element along the central longitudinal axis of the flow chamber for defining a flow passage through the flow chamber between the resistive element and the inner surface of the flow chamber, wherein the flow chamber conditions the fluid flow for accurate sensing of the flow over a range of fluid flow through the housing. A pressure sensor is disposed within the housing, the pressure sensor is in fluid communication with the first opening and the second opening for sensing a pressure differential between the first opening and the second opening and producing an electric signal in response to fluid flow through the housing, wherein the electric signal has a magnitude that corresponds with the rate of fluid flow through the housing and a sign that corresponds with the directionality of fluid flow through the housing. The system further comprises an individual breathing into the spirometer by exhaling or inhaling for flowing fluid through the spirometer from the first end to exit the second end, sensing flowing fluid within the spirometer to provide flow data according to the fluid flow, evaluating lung function according to the flow data, and using the lung function results to tailor specific, multi-media knowledge modules to the individual.

In one aspect of the digital treatment or rehabilitation program system, the multi-media knowledge modules are tailored to a specific disease or set of diseases. The medication dosing regimens are automatically or manually monitored.

In another aspect, software linked to spirometer provides a virtual avatar with whom the individual interacts, secure chat messaging, phone calls, or telehealth conferencing between the individual and any healthcare professional, or identifies and groups similar patients into virtual rehabilitation communities or virtual community support groups based on geopositional location, disease severity, track record of using the device, personality preferences, or any combination thereof.

In a further aspect, the virtual community support groups are able to communicate via secure group chat messaging, phone calls, or telehealth conferencing. The virtual community support groups have synchronized behavioral incentives, medication reminders, and task checklists. The virtual community support groups are able to congregationally communicate with a plurality of doctors, nurses, therapists, health coaches, or any combination thereof in real-time via secure group chat messaging, phone calls, or telehealth conferencing.

In a still further aspect, the software linked to the spirometer provides a behavioral incentive or disincentive, or a set of such behavioral incentives or disincentives, to the individual to improve adherence. The behavioral incentives or disincentives may include virtual, real, or transferable (i.e. virtual to real) rewards, achievements, coupons, currencies, cryptocurrencies, non-financial compensation, or any combination thereof at defined or randomized time intervals. The behavioral incentives or disincentives are selectively implemented by a plurality of learning algorithms that automatically adapt to the user's behavior or lung function results over time at defined or randomized time intervals. The behavioral incentives or disincentives may include animations, games, augmented reality, or any combination thereof whose functions are tied directly or indirectly to lung function readings.

In a further embodiment, a method is provided for remotely engaging individuals in clinical trials or research studies. The digital spirometry trial method comprises providing a spirometer for sensing fluid flow from the patient breathing through the spirometer. The spirometer comprises a tubular housing having an open first end and an open second end. The housing defines a fluid flow pathway extending between the first end and the second end, a first opening along the pathway and through which fluid flow enters, and a second opening longitudinally spaced along the pathway from the first opening and through which fluid flow enters. A flow chamber defining a fluid flow pathway is disposed within the housing between the first opening and the second opening. The flow chamber includes an elongated resistive element along the central longitudinal axis of the flow chamber for defining a flow passage through the flow chamber between the resistive element and the inner surface of the flow chamber, wherein the flow chamber conditions the fluid flow for accurate sensing of the flow over a range of fluid flow through the housing. A pressure sensor is disposed within the housing in fluid communication with the first opening and the second opening for sensing a pressure differential between the first opening and the second opening and producing an electric signal in response to fluid flow through the housing. The electric signal has a magnitude that corresponds with the rate of fluid flow through the housing and a sign that corresponds with the directionality of fluid flow through the housing. The method further comprises the steps of breathing into the spirometer by exhaling or inhaling for flowing fluid through the spirometer from the first end to exit the second end, sensing flowing fluid within the spirometer to provide flow data according to the fluid flow, evaluating lung function according to the flow data, using the lung function results to tailor specific, multi-media knowledge modules to the individual, and repeating these lung function tests over time and tracking their results.

In one aspect of the digital spirometry trial method, individuals who are already using the device are notified through the software associated with the device about ongoing clinical trials that they may be eligible for. Individuals can digitally sign an informed consent document to share their physiological and demographic information with a clinical trial sponsor, healthcare professional, or any other privileged individual linked to the study.

In a further aspect of the digital spirometry trial method, a plurality of non-spirometric information is collected via non-spirometric devices and shared by the individual alongside his or her personal lung function information.

In yet another aspect, the software linked to the spirometer provides a behavioral incentive or disincentive, or a set of such behavioral incentives or disincentives, to the study subject to improve adherence to study protocol. Lung function data may be automatically sent to a remote, secure server; aggregated with other study subject data; and analyzed.

In a still further aspect, individuals are compensated before the study, during the study, after the study, or any combination thereof. The individuals may be compensated based on personal or group adherence to a specific clinical trial protocol. Study subjects are compensated with virtual, real, or transferable (i.e. virtual to real) rewards, achievements, coupons, currencies, cryptocurrencies, non-financial compensation, or any combination thereof at defined or randomized time intervals.

BRIEF DESCRIPTION OF THE DRAWINGS

For a more complete understanding of the portable spirometer and method, reference should now be had to the embodiments shown in the accompanying drawings and described below, which are incorporated in and constitute a part of this specification. In the drawings:

FIG. 1 is an exploded perspective view of an embodiment of a portable spirometer.

FIG. 4 is a rear end elevation view of the portable spirometer as shown in FIG. 1 with a back cover removed.

DESCRIPTION

Figure 2A:
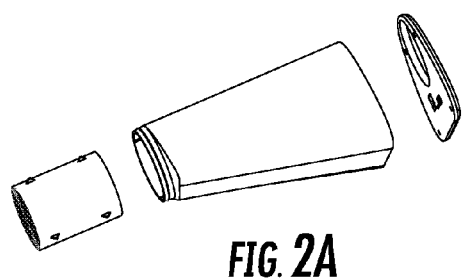
FIGS. 2A-2F are exploded perspective views of a housing for the portable spirometer as shown in FIG. 1.
Figure 2B:
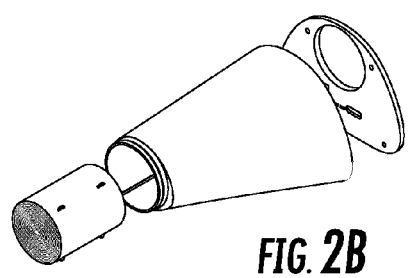
Figure 2C:
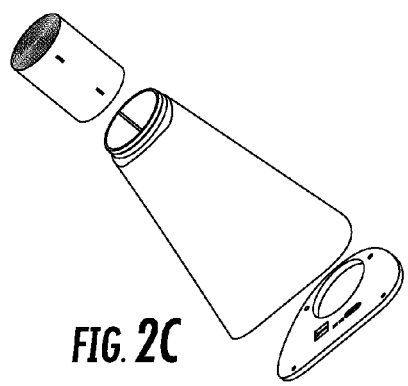
Figure 2D:
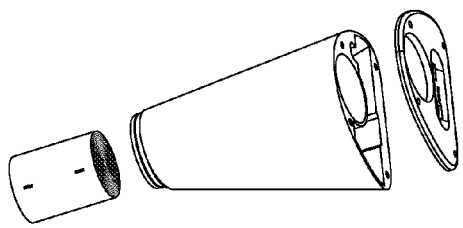
Figure 2E:
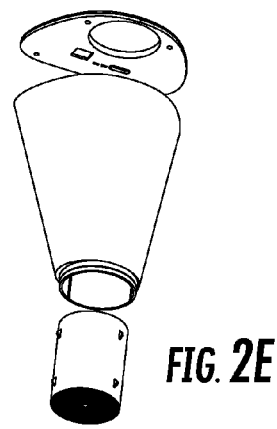
Figure 2F:
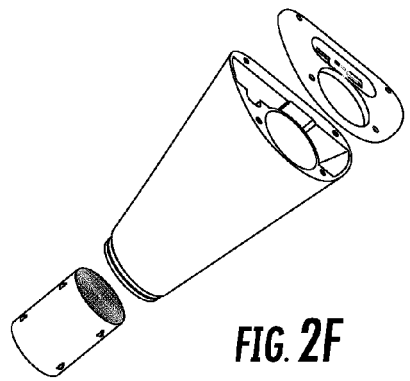

Referring now to the drawings, wherein like reference numerals designate corresponding or similar elements throughout the several views, an embodiment of a portable spirometer is shown in FIG. 1 and generally designated at 30. The spirometer 30 is configured to monitor respiration of an individual by measuring the amount of air inhaled and exhaled by an individual for a period of time. In one embodiment, the spirometer 30 interfaces directly with a computer or a smartphone application using either a physical connection or a wireless connection such that output data may be transmitted. The computer or smartphone may include an external display for providing fast and intuitive visualization of the output data without requiring additional manual input on the part of the user. In another embodiment, such an external display may provide real-time user feedback for ensuring correct usage of the spirometer for the full duration of the test. This arrangement simplifies the process of collecting and recording objective data on the condition of the user over time and better enables the user to manage their condition and comply with a treatment plan. More broadly, the spirometer 20 interface with the computer or smartphone application may further comprise a control system which, in turn, may be connected (e.g., wirelessly) to a healthcare provider, caregiver, and the like.

As shown in FIG. 1, the spirometer 30 comprises a hollow tubular housing 32 having a proximal end 40 and a distal end 42 and defining a fluid flow pathway and a hollow cylindrical mouthpiece 36 also having a proximal end 35 and a distal end 37. Referring to FIGS. 2A-2F, the housing 32 has a generally elliptical cross-section and tapers outwardly from the proximal end 40 to the distal end 42. It is understood that the housing 32 may take any shape, although the housing 32 is configured so as to be portable and thus preferably has a size and a shape that makes the spirometer 20 convenient to carry and handle and which may fit into a pocket or a protective pouch. As seen in FIG. 1, an outer diameter of a length of the proximal end 40 of the housing 32 is externally threaded 45. The proximal end 40 of the housing 32 receives the distal end 37 of the mouthpiece 36 which seats against the shoulder for mounting the mouthpiece 36 to the housing 32. The inner diameter of the mouthpiece 36 is the same as the diameter of the fluid flow pathway which is of constant diameter through the length of the housing 32. The mouthpiece 36 is configured to fit comfortably within the anatomical parameters of the mouth to ensure easy inhalation and exhalation maneuvers. In this arrangement, the mouthpiece 36 allows the user to inhale or exhale through the fluid flow pathway of the housing 32. The mouthpiece 36 can be either reusable or disposable and replaced for each user of the spirometer 30.

Figure 5A:
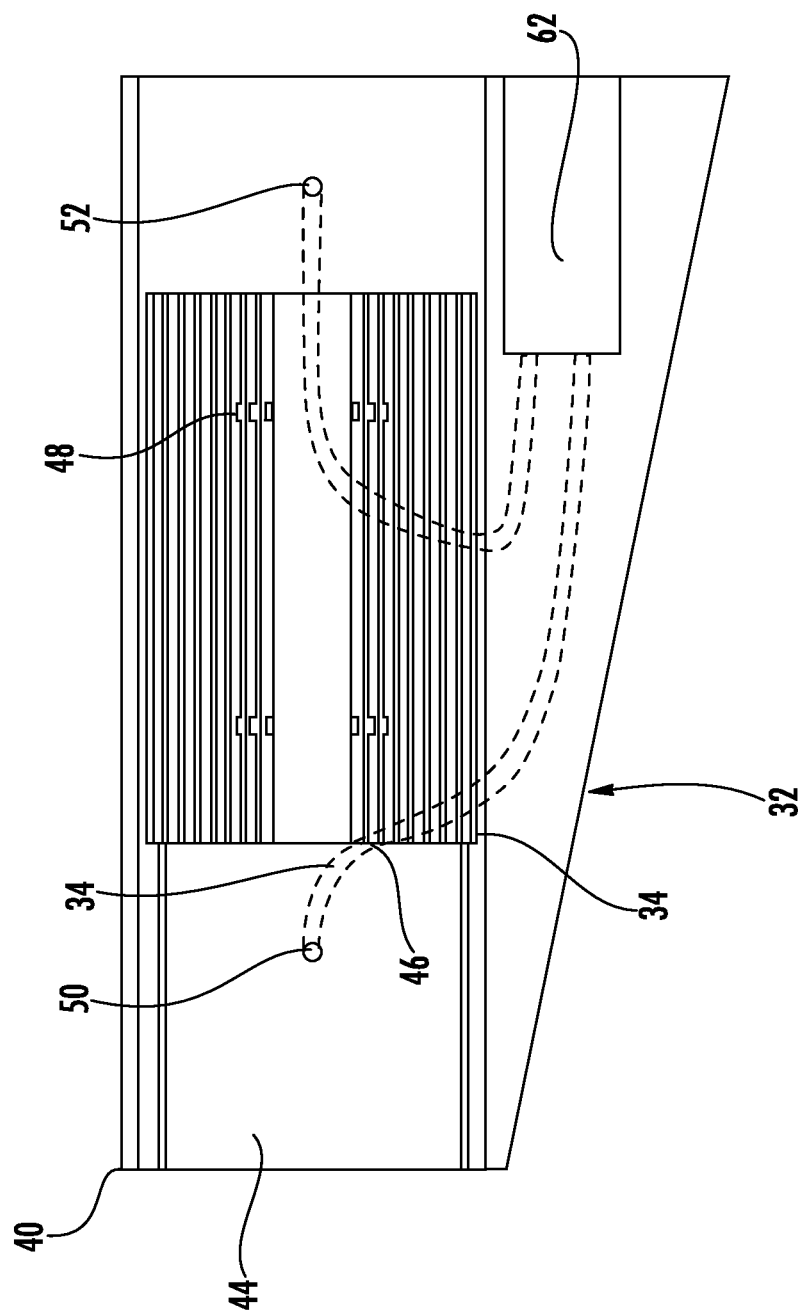
FIG. 5A is a longitudinal cross-section view of the of the portable spirometer as shown in FIG. 1.
Figure 5B:
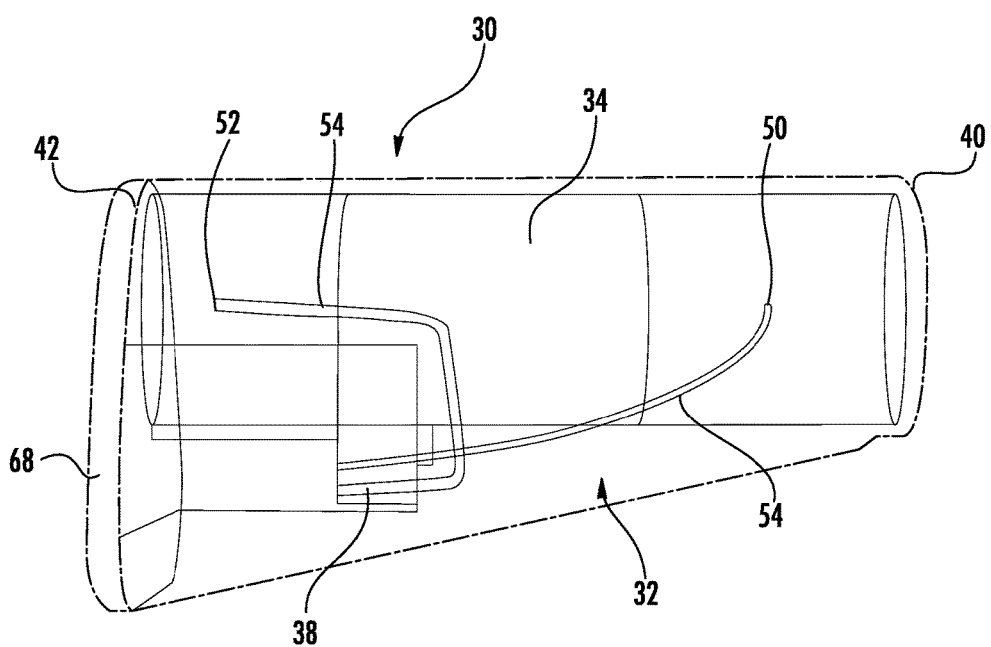
FIG. 5B is a side elevation of the housing for the portable spirometer as shown in FIG. 1 with the housing shown in phantom.
Figure 5C:
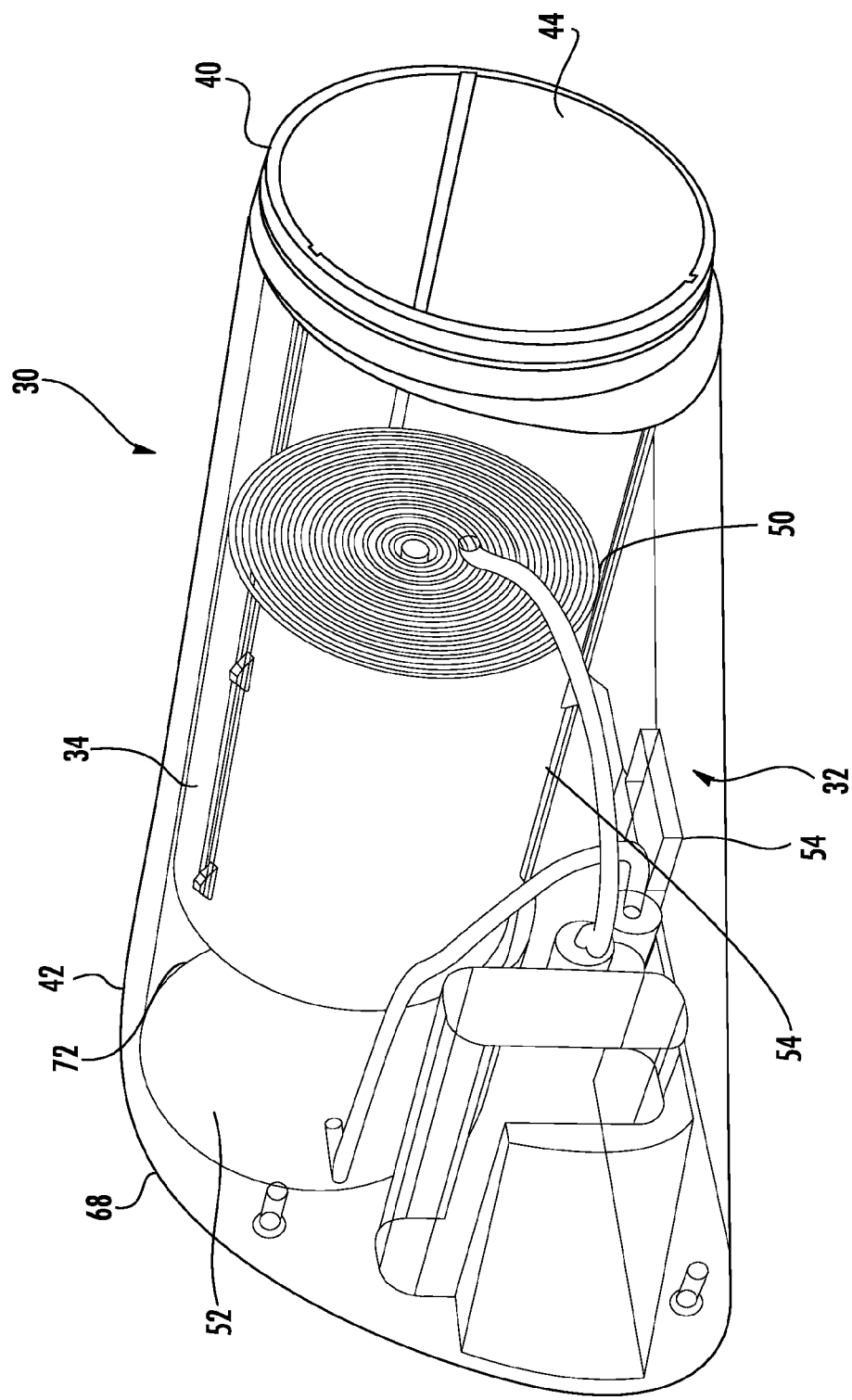
FIG. 5C is a front perspective of the housing for the portable spirometer as shown in FIG. 1 with the housing shown in phantom.

As shown in FIGS. 5A-5C, the fluid flow pathway of the housing 32 accommodates a flow chamber 34 spaced from the proximal end 40 of the housing 32. The flow chamber 34 is a generally cylindrical member and comprises a plurality of cylindrical concentric walls 46, or tubes, defining air flow passages extending in a direction substantially parallel to the longitudinal axis of the housing 32. The concentric walls 46 are joined at points along their length by branched flow passages 48 extending perpendicular to the direction of air flow through the tubes. The branched flow passages 48 also provide structural support to the tubes relative to one another and to the peripheral wall of the flow chamber 34. These structural branched flow passages 48 may be placed at any location throughout the longitudinal axis of the plurality of cylindrical concentric cylinders. In the embodiment shown, the flow passages 48 are placed at two locations midway along the cylinders.

Figure 12A:
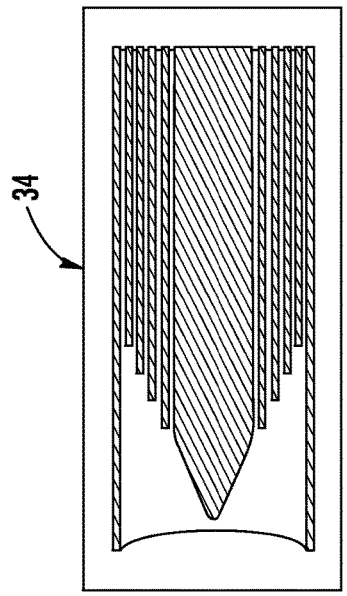
FIGS. 12A-12D show longitudinal cross-section views of different embodiments of a measurement flow chamber for the portable spirometer as shown in FIG. 1.
Figure 12B:
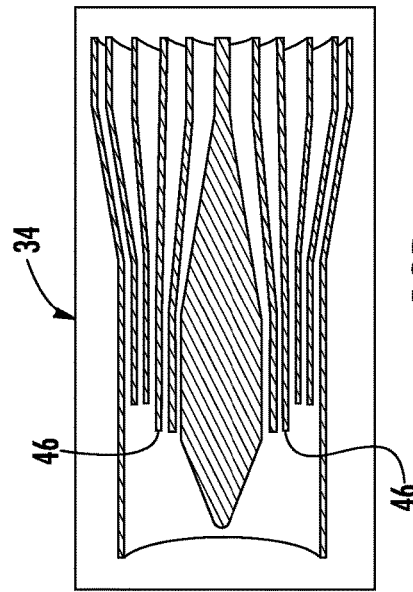
Figure 12C:
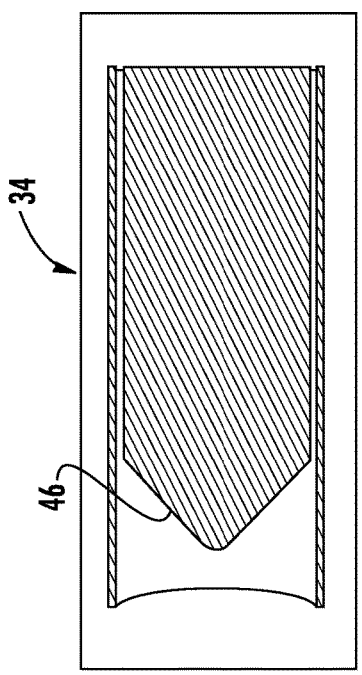
Figure 12D:
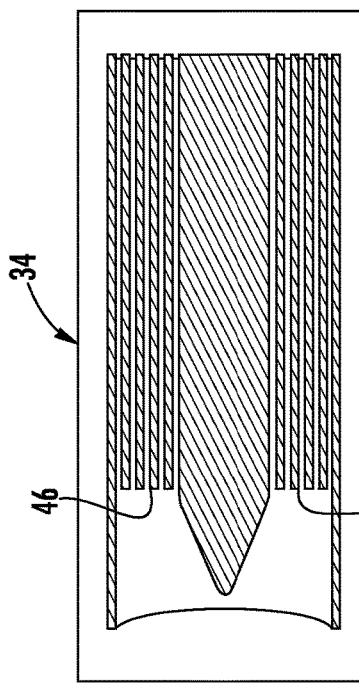

The number of passages, or annular regions, in the flow chamber 34 may vary. For example, referring to FIG. 12A, an embodiment of the flow chamber 34 is shown having a single air flow passage. FIG. 12B is the same embodiment of the flow chamber 34 as shown in FIGS. 5A-5C, wherein the concentric walls 46 define five passages and wherein the proximal ends of the walls 46 align with one another. Alternatively, the ends of the concentric walls 46 may be variously aligned. In FIG. 12C, the proximal ends of the cylindrical walls 46 may be staggered. Where the concentric cylindrical walls 46 are parallel, the passages may have a constant circular cross section. In other embodiments, the cross-sectional shape and area of the passages may vary along their length. For example, referring to FIG. 12D, the walls 46 diverge distally such that cross-sectional area of the passages gradually increase from their proximal end to their distal end. In alternate embodiments, have the passages similarly gradually decrease in area, or some passages may increase in area and others decrease. Alternative embodiments may utilize different variations in the lengths and shapes of the concentric walls 46.

Figure 15:
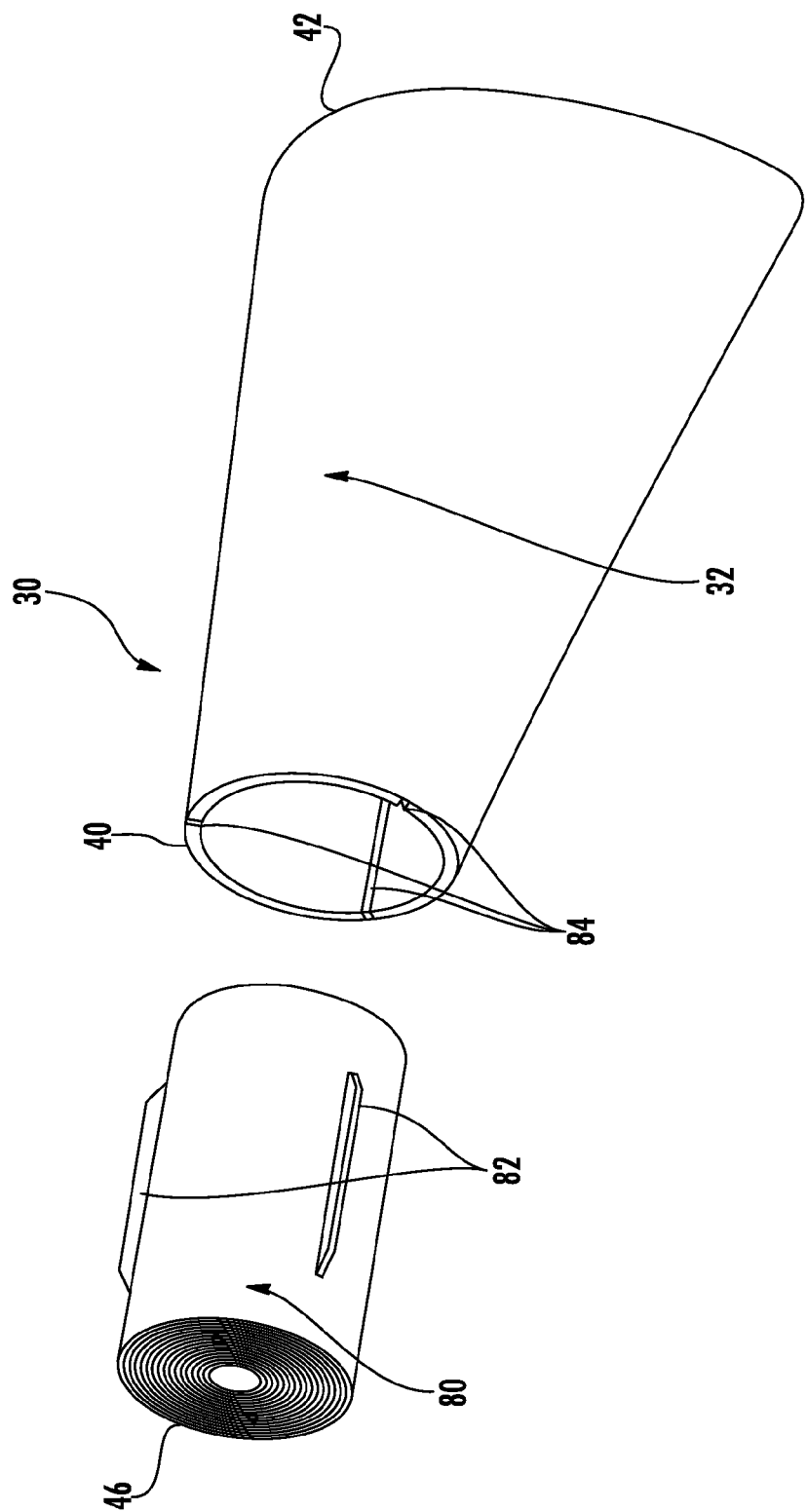
FIG. 15 is an exploded side perspective view of a second embodiment of a portable spirometer.

Another embodiment of a housing and flow chamber is shown in FIG. 15 and generally designated at 80. In this embodiment, the flow chamber has a plurality of radial fins 82 circumferentially spaced on the periphery of the flow chamber 34. The fins 82 are configured to be received in axial slots 84 defined in the housing 32.

As seen in FIGS. 5A-5C, the fluid flow pathway of the housing 32 defines at least a first fluid inlet opening 50 and a second fluid inlet opening 52 longitudinally spaced from the first fluid inlet opening 50. The first fluid inlet opening 50 is positioned between the proximal end 40 of the housing 32 and the proximal end of the flow chamber 34. The distance of fluid flow inlet opening 50 is chosen as to maximize the probability of capturing fully developed flow velocity and pressure profiles at that point while minimizing the capture of any turbulence created by the fluid obstructing insert walls 46. The first fluid inlet opening 50 extends in a direction perpendicular to the longitudinal axis of the housing 32. Air flow passing from the mouthpiece 36 into the housing 32 passes over the first fluid inlet opening 50. The second fluid inlet opening 52 is positioned between the distal end 35 of the flow chamber 34 and the distal end 42 of the housing 32. The distance of the second fluid flow inlet opening 52 is chosen as to maximize the probability of capturing fully re-developed flow velocity and pressure profiles at that point, having re-converged after passing through the fluid obstructing insert of the flow chamber 34, while minimizing the capture of any turbulence created by the fluid obstructing insert. The second fluid inlet opening 52 extends from the flow chamber 34 in a direction perpendicular to the longitudinal axis of the housing 32. Fluid exiting the passages 46 of the flow chamber 34 passes over the second inlet opening 52. When fluid flow is reversed during an inhalation versus an exhalation maneuver, the first and second fluid inlet openings 50, 52 will capture complementary but reversed snapshots of the pressure profiles at their respective locations, thereby creating a differential pressure of equal but negative magnitude. This embodiment of the spirometer 30 thus can account for bi-directional flow measurement.

Figure 13:
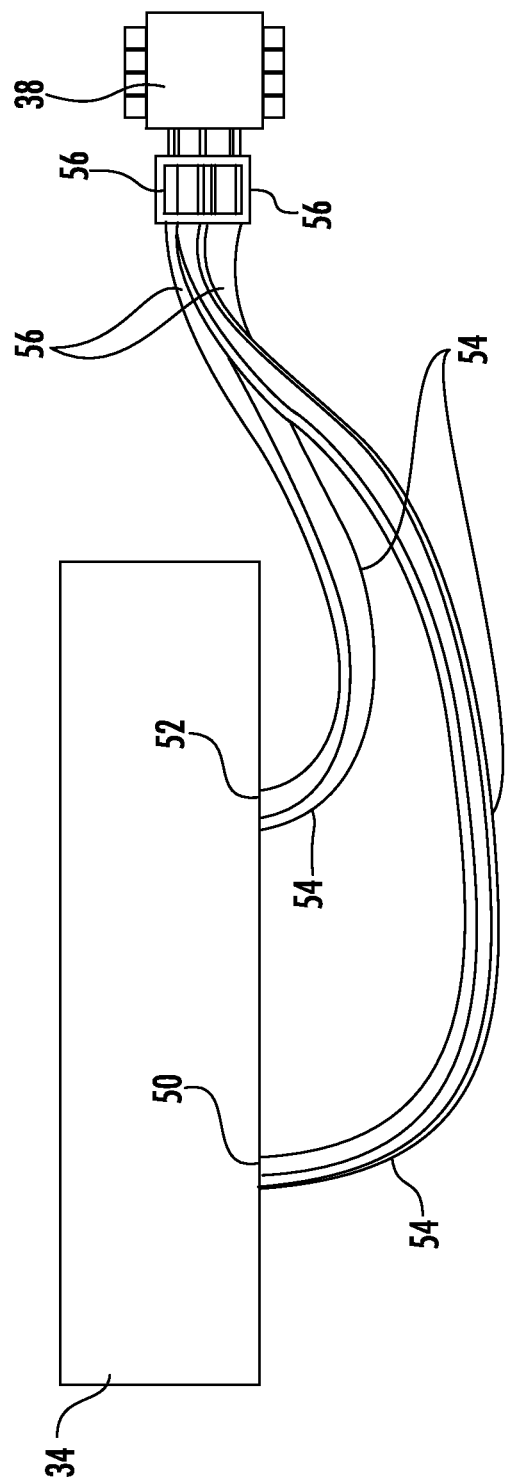
FIG. 13 is a schematic top plan view of an embodiment of a connection between a flow chamber and a differential pressure sensor for the portable spirometer as shown in FIG. 1.
Figure 14:
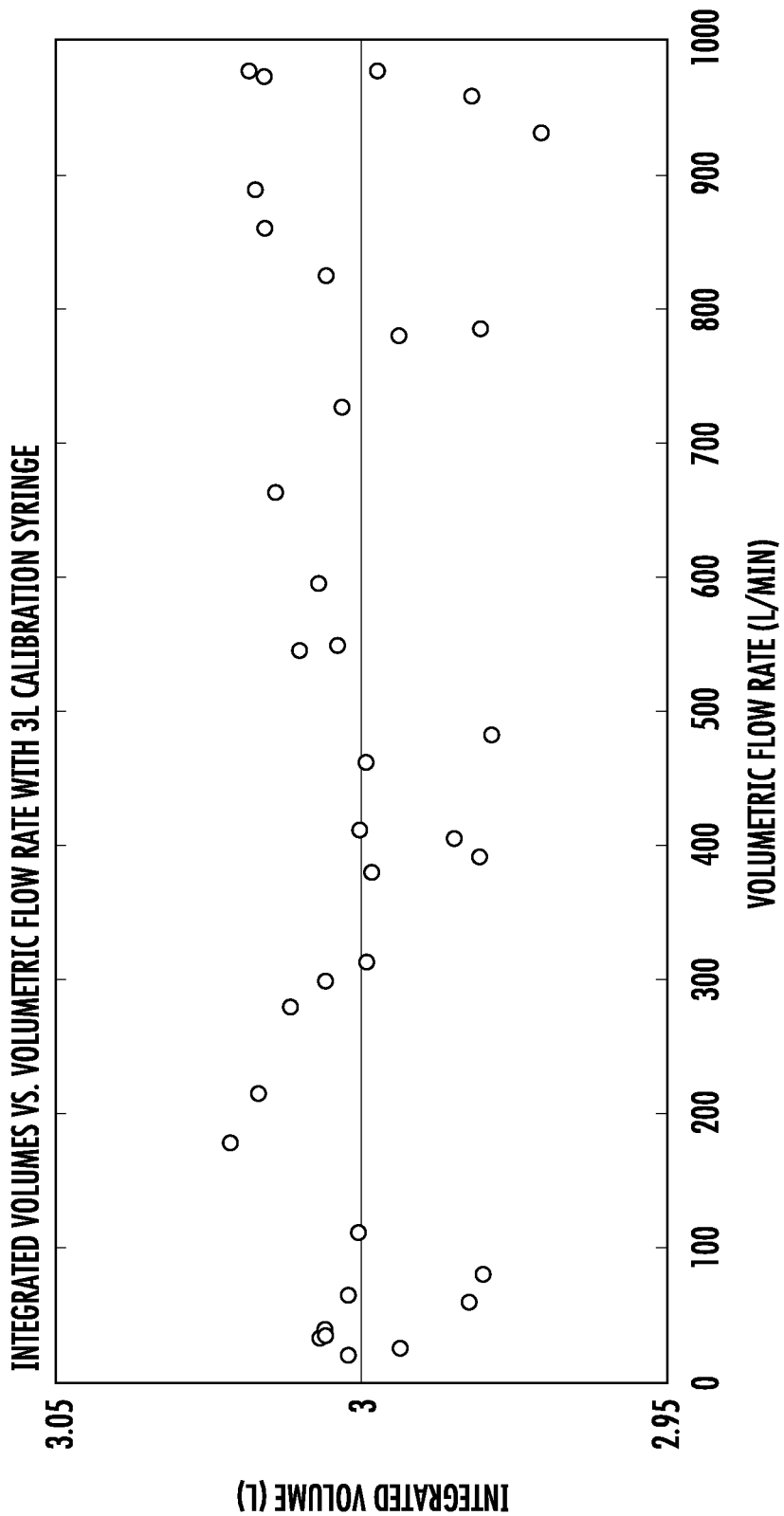
FIG. 14 is a graph showing test data from the portable spirometer as shown in FIG. 1.

Referring to FIG. 13, the first fluid inlet opening 50 and the second fluid inlet opening 52 are separately connected via dedicated fluid flow tubes 54 to input measurement points of a differential pressure sensor 38. In one embodiment, the differential pressure sensor 38 comprises a transducer. The differential pressure sensor 38 is disposed in the distal end of the housing 32 opposite the mouthpiece 36. The air flow tubes 54 internally connect the points at which the pressure in the cavity is measured to the inputs of the differential pressure transducer 38. The separate inputs of the pressure transducer 38 are sealingly connected to the tubes 54 via short connectors 56 to guard against pressure loss due to air escaping. In one embodiment, the connectors 56 are made of vinyl tubing and in other embodiments may be affixed directly with adhesives. As shown in FIGS. 2A-3, the tubes 56 may open through holes in a distal end wall 58 of the housing 32. Thus there is fluid communication between the housing 32 on either side of the flow chamber 34 and the differential pressure sensor 38.

In other embodiments, other arrangements of the air flow inlet openings are contemplated and air pressure may be measured at more than one point around the circumference of the flow chamber in order to average local pressure fluctuations. In addition, there may be sub-channels connecting the individual sets of measurement points as long as fluid communication between the first and second air flow inlet openings 50, 52 utilize a continuously connected path between the flow chamber 34 and the pressure sensor 38.

Figure 3A:
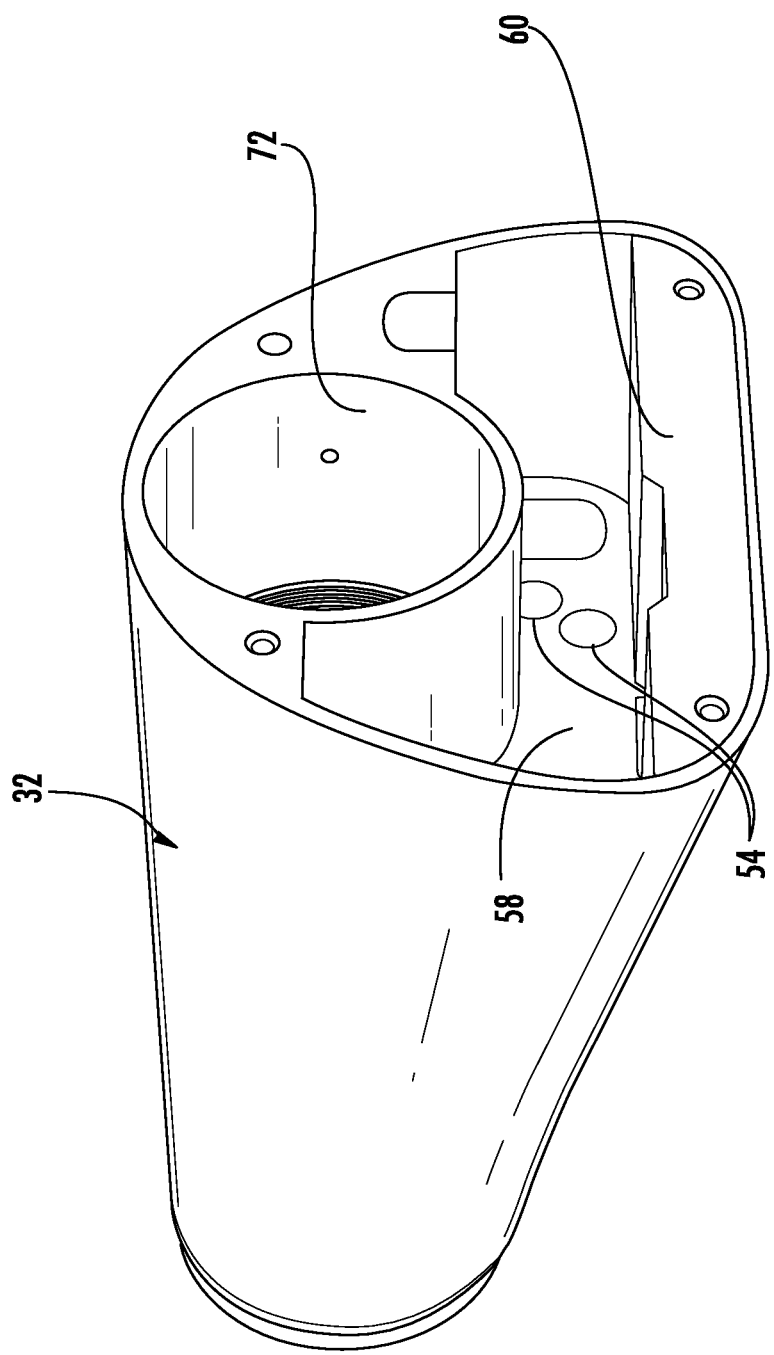
FIG. 3A is a rear perspective view of the portable spirometer as shown in FIG. 1.
Figure 3B:
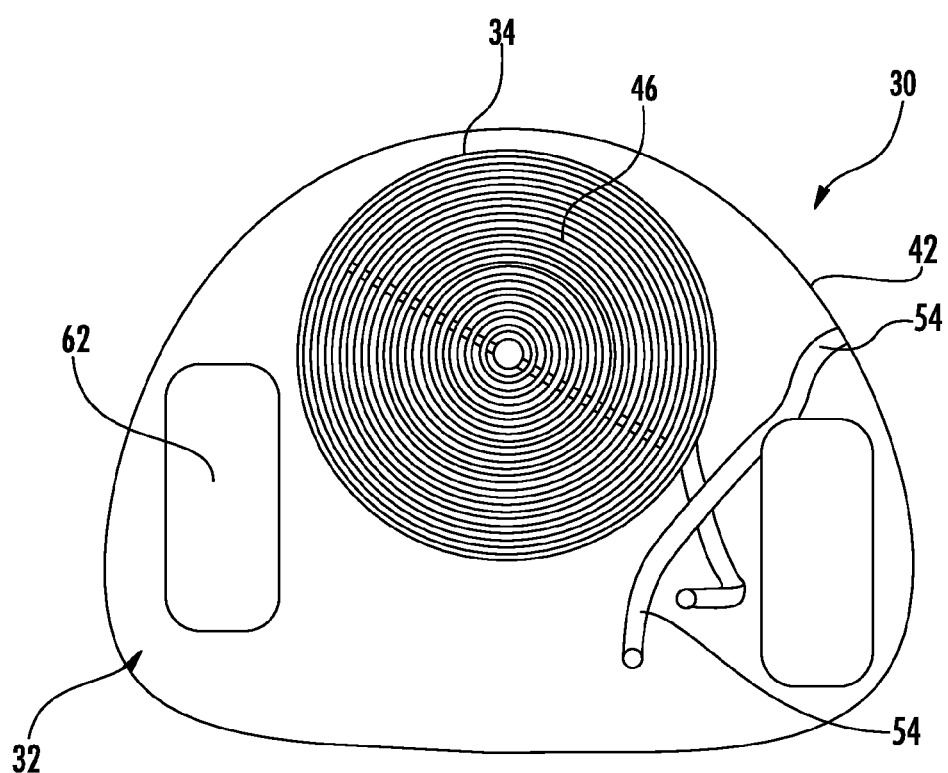
FIG. 3B is a rear transverse cross-section view of the portable spirometer as shown in FIG. 1.
Figure 3C:
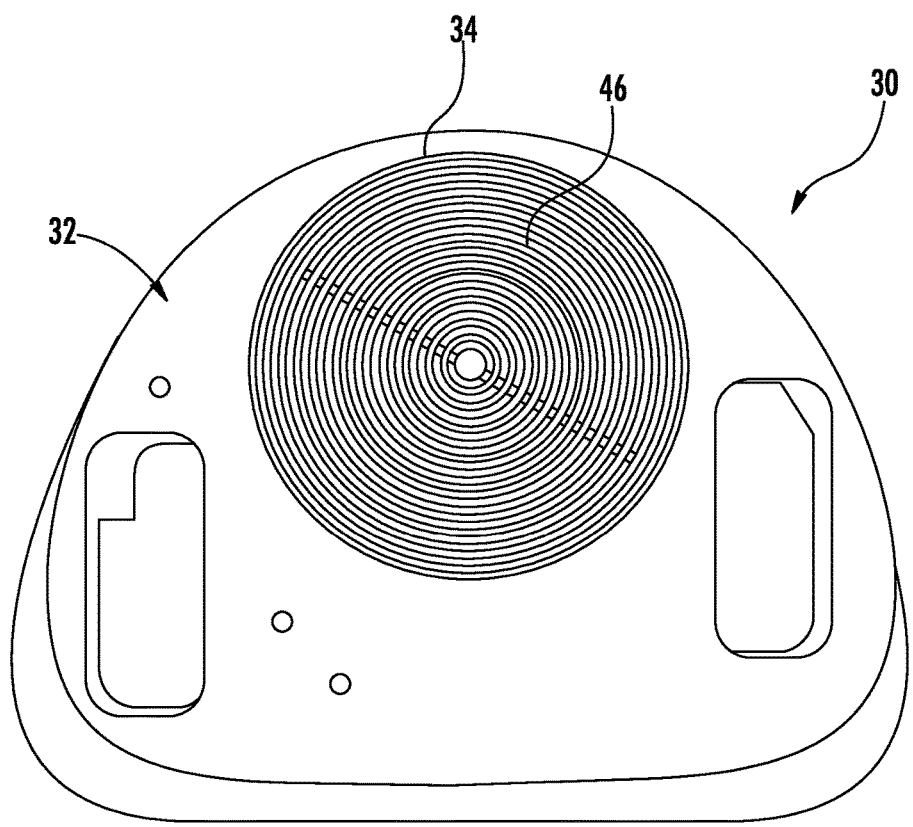
FIG. 3C is a front transverse cross-section view of the portable spirometer as shown in FIG. 1.

Referring to FIGS. 3A, 3B and 4, the distal end of the housing 32 is configured to house the electronics necessary for operation of the spirometer 30. An electronic circuit associated with the spirometer is on a printed circuit board (PCB) mounted beneath the outlets for the tubes 54. In one embodiment, a PCB 60 is employed that is made according to FR4 170Tg/290Td standards, containing woven fiber-glass, flame resistant epoxy resin, ENIG (gold) finish, with copper traces. The differential pressure sensor 38 is attached to the PCB 60. A removable lithium battery fits into a slot 62 in the end wall 58 of the housing 32 and is operatively connected for providing power to the PCB 60. The battery may be rechargeable via a USB 64 or other suitable means. It is understood that other power means such as photovoltaic, capacitance, energy harvesting, combinations thereof, and the like may be used instead of or in addition to the battery. However, a battery is preferred for portability of the spirometer 30.

The components of the spirometer 30 may be produced by a number of methods, including for example, three-dimensional printing or injection molding, preferably from a lightweight plastic material. The housing 32 and the mouthpiece 36 of the spirometer 30 in their current embodiments are manufactured using either acrylonitrile butadiene styrene (ABS) or polylactic acid (PLA) plastics, which are then 3D printed into the desired shape. Suitable alternative materials include other plastics, preferably biocompatible; glass; metals; or other relatively durable and lightweight material. In one embodiment, the spirometer 30 is constructed such that it has a clear front end and back end.

The spirometer operates on the basis of the Hagen-Poiseuille equation, which describes a linear relationship between pressure and flow velocity in its formulation, according to which the pressure drop Op in an incompressible, frictional Newtonian fluid undergoing laminar flow in a pipe can be expressed as:

$$Op = (32\mu L v)/(gPd^2)$$

where $\mu$ is the dynamic viscosity, L is the length of the pipe, v is the fluid velocity, g is the gravitational constant, P is the fluid density, and d is the diameter of the pipe. Since air is a close approximation to an incompressible, frictional Newtonian fluid, the goal is thus to reduce the Reynolds number, Re, so as to produce laminar flow (which occurs for Re<2200). The Reynolds number can be computed as follows:

$$Re = QD_H/vA$$

where A is the cross-sectional area of the tube, v is the kinematic viscosity, Q is the volumetric flow rate, and DH is the hydraulic diameter of the pipe.

Thus, it is possible to decrease the Reynolds number by decreasing the hydraulic diameter. In addition, we note that passing the fluid being measured through multiple concentric tubes reduces the volumetric flow rate through any single tube, doubly decreasing the Reynolds number, while approximately maintaining the total cross-sectional area of the flow when the concentric walls 46 are thin. Thus, by passing the fluid through multiple concentric tubes and reducing the hydraulic diameter, laminar flow can be achieved across a wide dynamic range of input flow rates and create a pressure drop that is linearly proportional to the fluid velocity, as modeled by the Hagen-Poiseulli equation.

The spirometer 30 is thus configured to produce a substantially laminar flow of air across a wide dynamic range of flow inputs that are normally observed in inhalation and exhalation maneuvers. The configuration acts on the fluid flow so that the fluid flow is converted to a more consistent flow profile. The location of the flow chamber 34 between the open proximal end 40 of the housing 32 and the flow sensor 38 at the distal end 42 of the housing 22 linearizes air flow across a range of flow rates causing the flow of air generated by a user at the mouthpiece to become a laminar stable air flow in the midsection area, inclusive of the locations of fluid flow inlets 50 and 52. By configuring the spirometer 30 to convert and maintain the air to a substantially laminar flow for at least the fluid flow path, the spirometer 30 is capable of producing a consistently accurate response independent from outside factors and inhalation or exhalation patterns.

Figure 6:
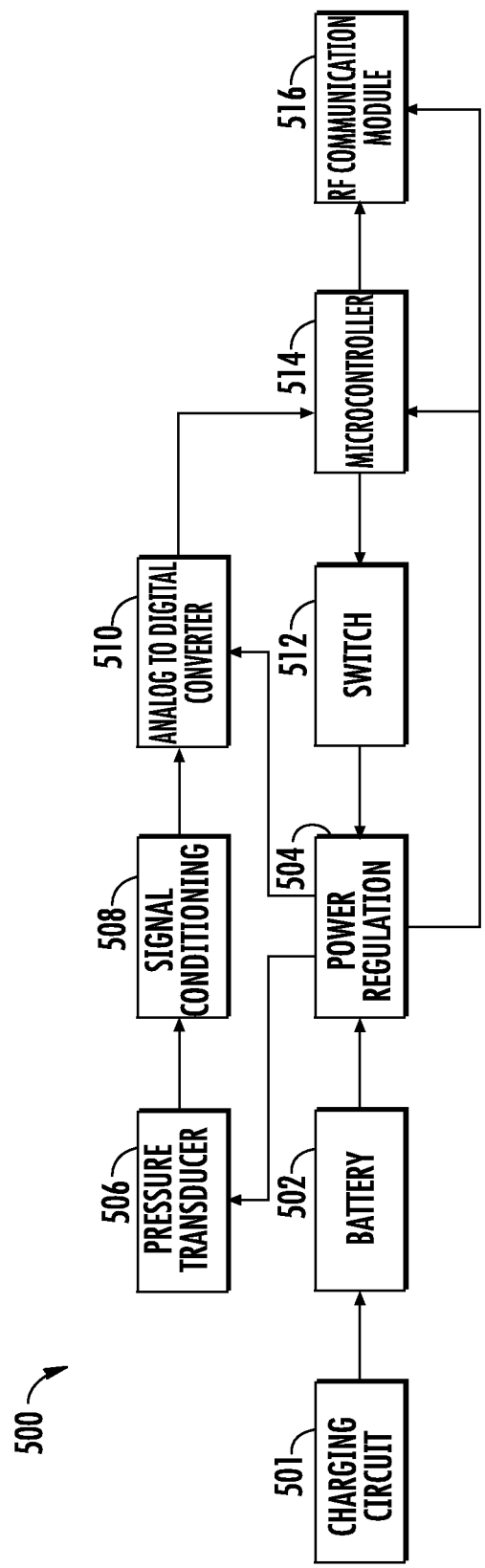
FIG. 6 is a block schematic diagram of an example of an electronic system in a spirometer for processing the data collected from a flow chamber of the spirometer in accordance with an embodiment.

FIG. 6 is a block schematic diagram of an example of an electronic system 500 in a spirometer for processing the data collected from a flow chamber of the spirometer in accordance with an embodiment of the present invention. The electronic system 500 includes a charging circuit 501 for charging a rechargeable battery 502. In accordance with an embodiment, the rechargeable battery is a lithium battery although other type rechargeable batteries, non-rechargeable batteries, or sources of electrical power are also useable. The battery 502 is electrically connected to a power regulation circuit 504 that conditions or regulates the electrical power from the battery 502 and supplies the regulated electrical power to a differential pressure transducer 506. The differential pressure transducer 506 measures air pressure, which is converted to an air flow rate, from a user in the flow chamber and coverts the air pressure measurements or air flow measurements to corresponding electrical signal that represent data containing the air pressure or flow measurements. A signal conditioning circuit 508 receives the electrical signals from the differential pressure transducer 506 and an analog-to-digital converter (ADC) 510 receives the conditioned electrical signals from the signal conditioning circuit 508. The ADC 510 samples the electrical signals and generates digital signals representing the air pressure or flow measurement data from measurements in the flow chambers. The ADC 510 also received electrical power from the power regulation circuit 504.

A microcontroller 514 receives the digital air measurement data from the ADC 510. The microcontroller 514 controls a switch 512 based on the digital air measurement data from the ADC 510. The switch 512 controls operation of the power regulator in supplying electrical power to the differential pressure transducer 506 and the ADC 510. The microcontroller 514 is also connected to an RF communications module 516 for wirelessly transmitting the digital air pressure or flow measurement data to a computing device, mobile communications device or other device for further processing the air pressure measurement data, storing and/or displaying the air pressure measurement data. It is contemplated that other device embodiments may perform such calculations onboard the device itself without wireless transmission.

Figure 7:
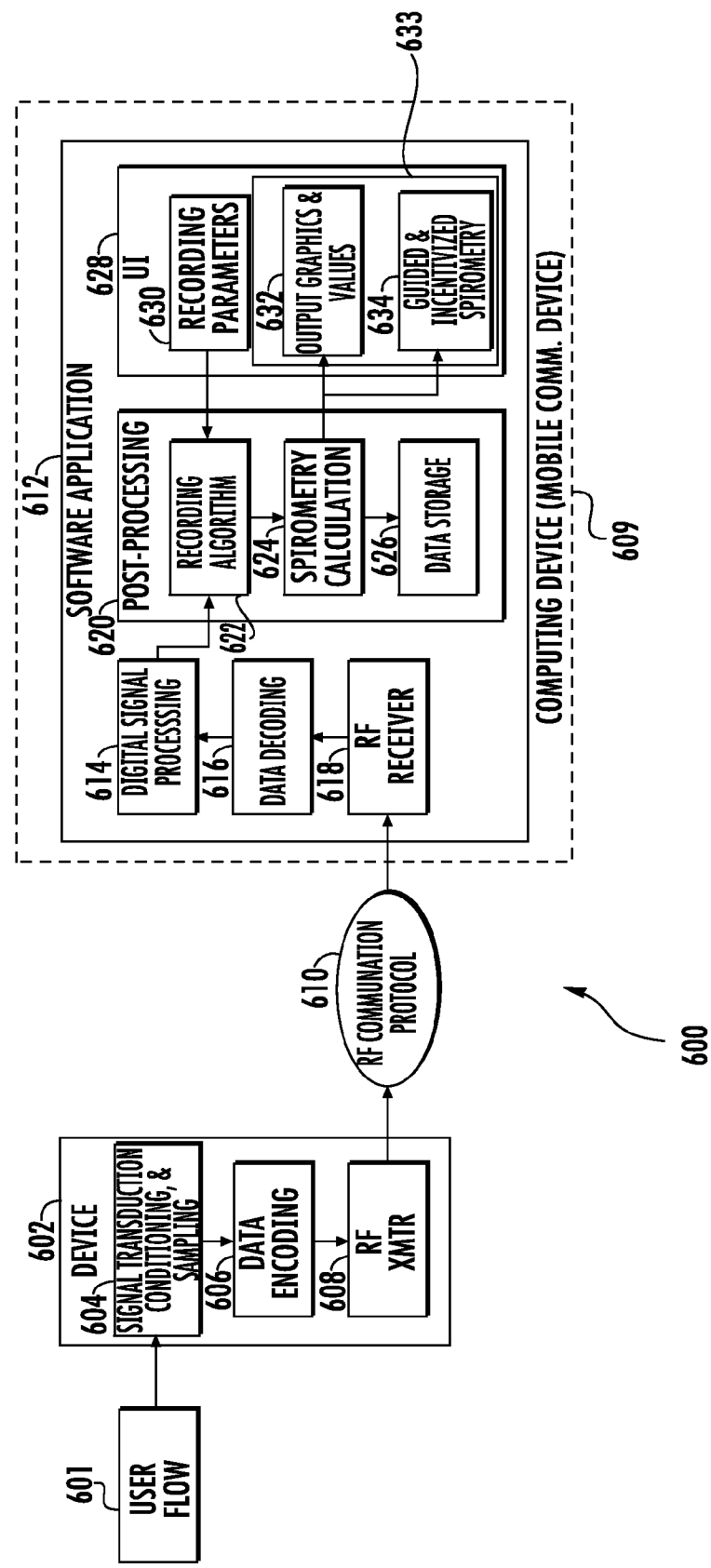
FIG. 7 is a flow chart of an example of a method for processing the data collected from the flow chamber of the spirometer in accordance with an embodiment.

FIG. 7 is a flow chart of an example of a method 600 for processing the data collected from the flow chamber in accordance with an embodiment of the present invention. In block 601 air pressure or flow measurements are collected from the user as an input to the system. The device 602 processes the air pressure or air flow from the user. In block 604, the air pressure or air flow measurements are transduced, conditioned, and sampled. In accordance with the embodiment previously described, the user's air pressure or flow input are transduced, conditioned and sampled by the pressure transducer 506, signal conditioning circuit 508, and sampled by the ADC 510.

In block 606, the transduced, conditioned, and sampled signals from block 604 are data encoded and are transmitted by an RF transmitter 608 to a computing device 609 for further processing, storing, and/or displaying the air pressure or flow measurement data. Such calculations may include further filtering of the signal for visualization or device utilization, such as Butterworth filtering or Kalman filtering, and mathematical integration of digitized flow rates to calculate lung volumes of the patient at defined intervals. As previously described, in accordance with an embodiment, the computing device 609 is a mobile computing device, mobile communications device or other device, and it is contemplated that other device embodiments may perform such calculations onboard the device itself without necessarily requiring wireless transmission. The encoded data may be transmitted using an RF communications protocol 610, such as Bluetooth protocol or any other wireless communications protocol, inclusive of cellular signals.

The air pressure or flow measurement data is received by an RF receiver 618 of the computing device 609. In block 616, the received air pressure or flow measurement data is decoded. In block 614, digital signal processing is performed on the decoded data.

In block 620, post-processing is performed. In accordance with an embodiment, post-processing includes blocks 622, 624 and 626. In block 622, a recording algorithm receives recording parameter 630. The recording parameters 630 may be entered by a user via a user interface (UI) 628. The recording parameters 630 include but are not necessarily limited to PEF, FEV1, and total exhaled volume.

In block 624, spirometry calculations are performed. The results of the spirometry calculations are presented as output graphics and values 632 on a display 633 of the user interface 628. In accordance with an embodiment, guided and incentivized spirometry 634 are also presented on the display 633 of the user interface 628. In block 626, the results of the spirometry calculations are also stored in a data storage device. The storage of the data may be on the computing device 609 itself, the device, or on an external server that may be connected wirelessly.

Figure 8:
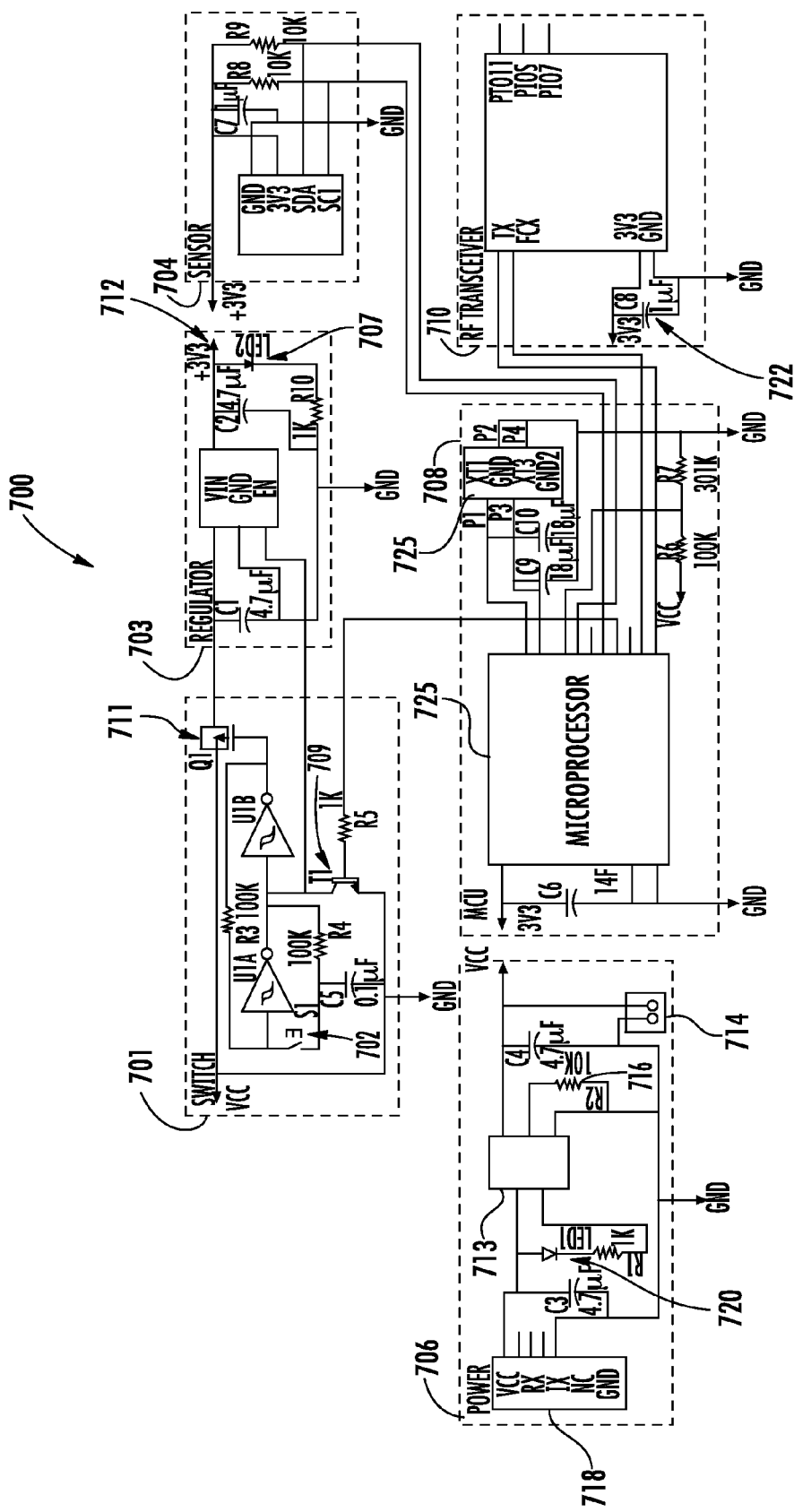
FIG. 8 is a schematic diagram of an example of an electronic system for processing data collected from a flow chamber of a spirometer in accordance with another embodiment.
Figure 9A:
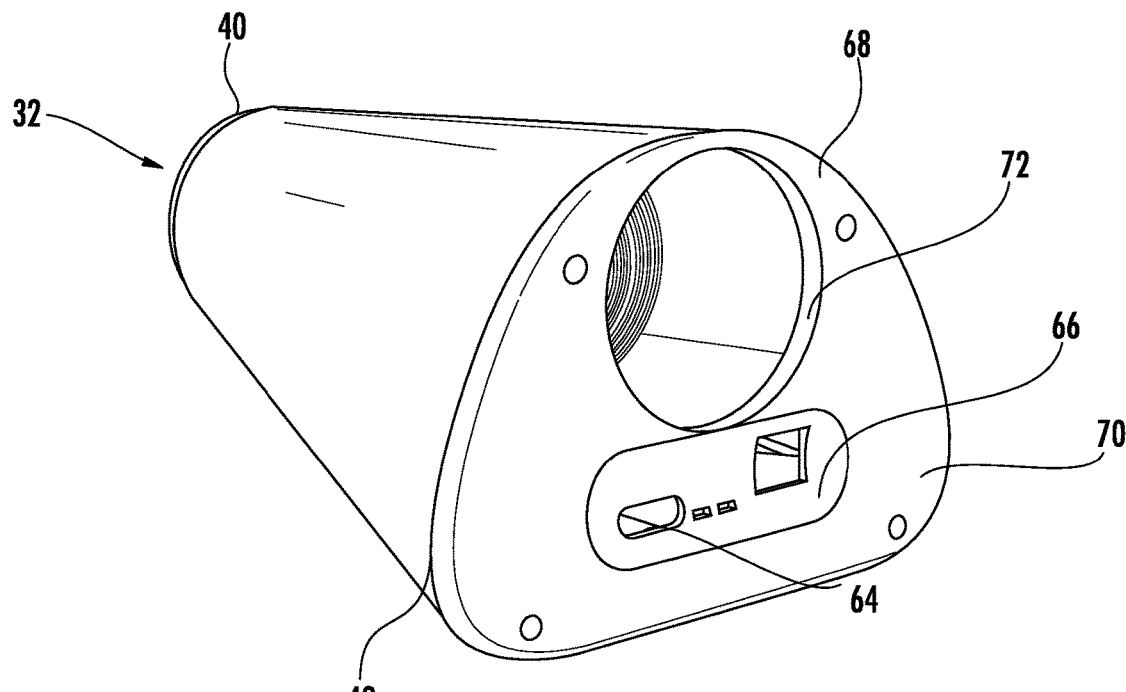
FIG. 9A is a rear perspective view of a housing for the portable spirometer as shown in FIG. 1.
Figure 9B:
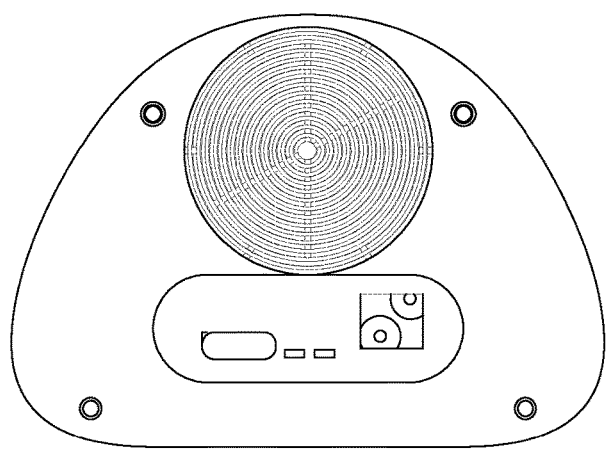
FIG. 9B is a rear elevation view of a housing for the portable spirometer as shown in FIG. 9B.

FIG. 8 is a schematic diagram of an example of the electronic system 700 for processing data collected from a flow chamber of a spirometer in accordance with an embodiment of the present invention. In the exemplary embodiment, the system 700 is used for the system 500 in FIG. 5. The electronic system 700 includes a switching circuit 701 that serves to connect and disconnect electrical power (VCC) from an electrical power source 706 to the remainder of the system 700. The switching circuit 701 corresponds to the switch 512 in FIG. 5. The switching circuit 701 may be manually operated via a button (S1) 702, or electronically via a voltage signal from a microcontroller 708 to transistor (T1) 709 of the switching circuit 701. A power transistor (Q1) 711 serves to start and stop flow of current from the electrical power source 706.

A voltage regulator 703 receives electrical power from the switching circuit 701. The voltage regulator 703 is connected to bypass capacitors C1 and C2. An indicator light (LED2) 707 serves to let the user know whether the device is on or off. The output (+3V3) 712 of the voltage regulator 703 powers the microcontroller 708, an RF transceiver 710 and a pressure sensor circuit 704. In accordance with an embodiment the RF transceiver 710 is a Bluetooth transceiver although any type transceiver is usable.

The digital pressure sensor circuit 704 includes an internal analog-to-digital (ADC) converter. In one implementation of the system 700, the microcontroller 708 communicates using an I2C protocol. Other implementations may include other forms of digital communication (e.g. SPI), or use an analog pressure sensor measured with a discrete analog-to-digital converter.

The electrical power source 706 includes a rechargeable lithium battery 713 connected to an electrical plug (JP1) 714, and provides electrical power (VCC) to the switch circuit 701. The rechargeable lithium battery 713 includes a lithium charging integrated circuit with a charging rate controlled by a resistor (R2) 716. A universal serial bus (USB) connector 718 is included to connect the system 700 to an external electrical power source to provide electrical power for charging the lithium battery 713. An indicator light (LED1) 720 serves to notify the user about the status of the battery charging.

The microcontroller circuit 708, which draws electrical power from the voltage regulator 702, receives data from the pressure sensor 704, and transmits the data to the RF transceiver 710. The microcontroller 708 also measures the voltage of the battery 713 through a voltage divider formed by resistors R6 and R7, and electrically switches off the electrical power if battery voltage levels are too low in transistor (T1) 709 of the switching circuit 701. A crystal 720 connects to the microcontroller 708 and provides a high-precision operating frequency signal.

The RF transceiver 710 receives measurement data from the microcontroller circuit 708. The RF transceiver 710 is connected to decoupling capacitor (C8) 722. As previously described the RF transceiver 710 transmits the air pressure measurements or air flow measurements to a computing device, such as computing device 609 in FIG. 6, for further processing, storing and/or presentation to a user as described herein.

In use, the mouthpiece 36 of the spirometer 30 is inserted into the proximal end 40 of the housing 32. A mechanical push-button switch 66 is centrally located on a rear cover 68 adjacent to two LED's 70 that display green or red when illuminated. When using the spirometer 30, the user first actuates the switch 66 for turning on the spirometer 30. The green LED will illuminate when the switch 66 is actuated indicating that the spirometer 30 is powered on. If the green LED is off, the spirometer 30 has run out of battery charge and should be charged via the USB micro connector 64 accessible through the cover plate 68. While the battery is charging, the red LED will turn on to indicate that the battery is being charged. The spirometer 30 may be used while the battery is charging.

Figure 10:
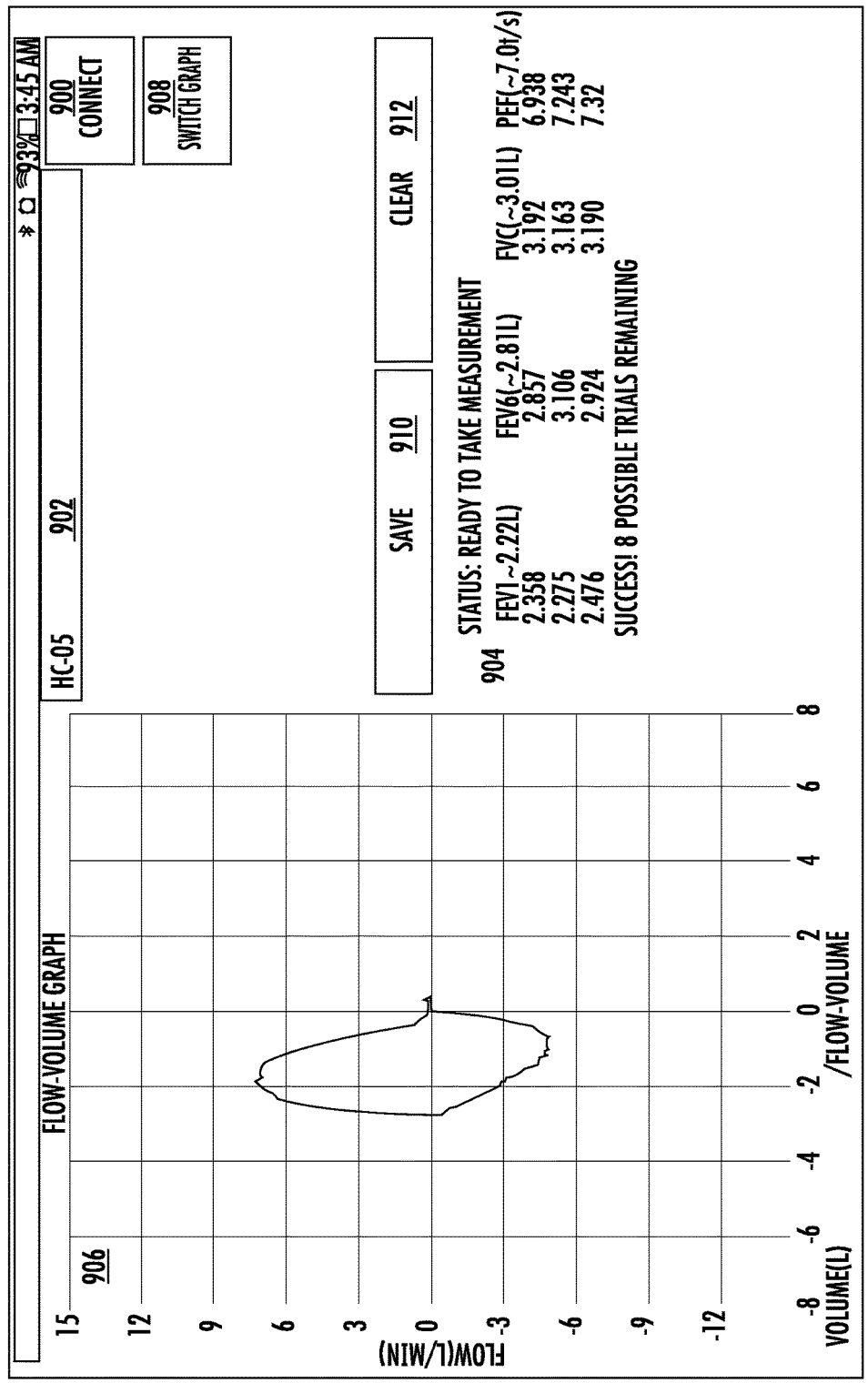
FIG. 10 shows a screenshot of example data collected using the portable spirometer as shown in FIG. 1 as displayed on a graphical interface of a mobile application.
Figures 11A, 11B:
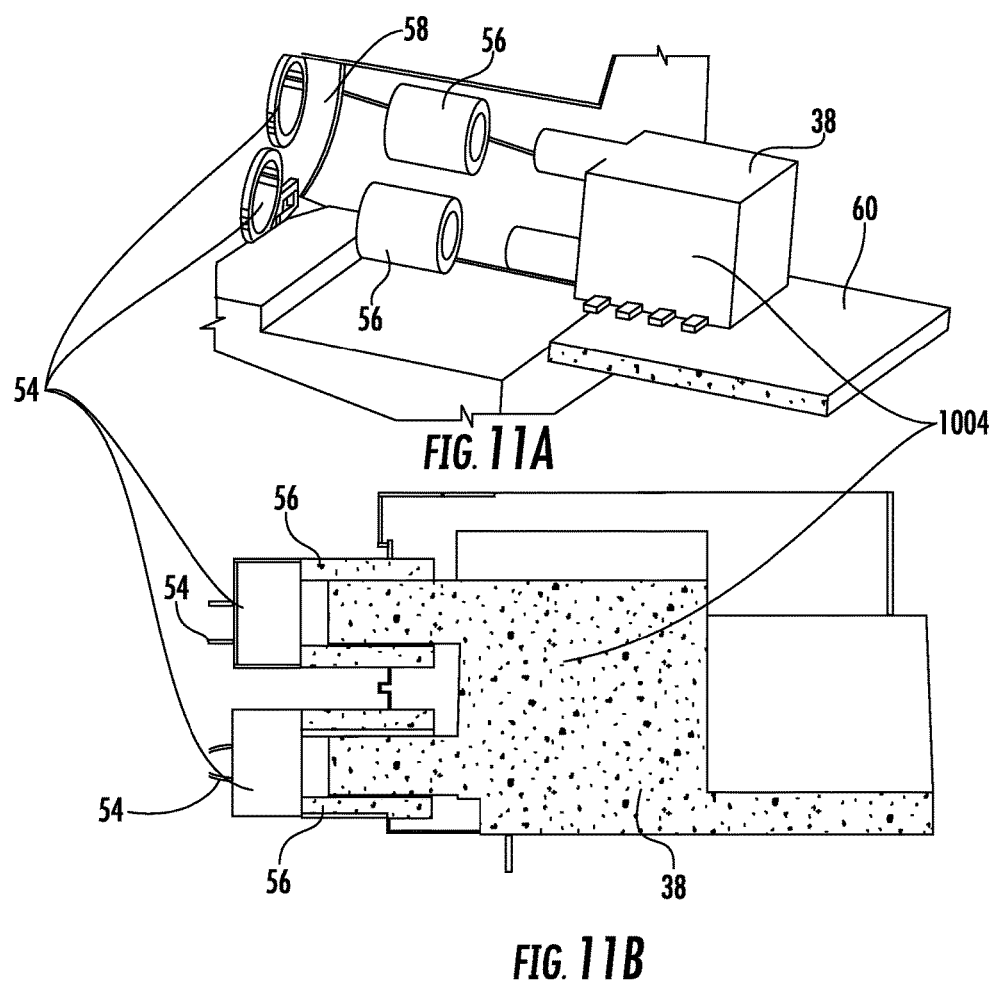
FIGS. 11A and 11B are an exploded side perspective and a longitudinal cross-section view, respectively, of a portion of the housing for the portable spirometer as shown in FIG. 1 showing a connection between the electronic circuit, including differential pressure transducer, and the housing.

When the spirometer 30 has been powered on, the user should then select the Bluetooth device on the interface of the mobile application (FIG. 10) corresponding to the device. The available Bluetooth device, labeled in this example as HC-05, is indicated at 902. Once the device is selected, the user pairs the mobile application with the spirometer by pressing 'Connect' at 900. After the device is paired with the application, data collected from the device appears in parts 904 and 906. Data may be cleared using part 912, or saved using part 910.

With the spirometer 30 paired with the mobile application, the user inhales sharply through the mouthpiece 36 at the proximal end 40 of the housing 32 and exhales forcefully. The airflow from the user's breath passes through the mouthpiece 36 and into the proximal end 40 of the housing 32. The housing 32 functions to funnel air flow into the concentric cylindrical passages of the flow chamber 34 creating a measurable pressure change. Air flow exits the housing through the outlet opening 72.

The spirometer 30 can be used to measure and provide as output data any of a number of clinical metrics for lung performance parameters, including but not limited to, forced expiratory volume (FEV) at timed intervals such as the FEV1 (one second) test, FEV6 (six second) test, FVC (forced vital capacity), forced expiratory flow (FEF) such as FEF 25-75, and PEF, many of which are displayed at 904. The rate of flow of the user's breath as a function of the volume exhaled by the user is displayed at 906. This graph is referred to as a flow-volume curve, and is commonly used in clinical practice. In addition, the user may opt to view a graph of the rate of flow of the user's breath as a function of time by selecting 908. In the one embodiment, the mobile computing device is capable of performing an analysis for each expiration and will display these results on its own screen; however, it is contemplated that other embodiments can perform the same spirometric analyses onboard the device and communicate these results wirelessly.

The spirometer 30 is configured to be coupled to an external display device by a physical connection or a wireless connection. The display device may be an external processing unit, such as a smartphone or personal computer, permitting the user to transfer data from the spirometer 30 and display the results on a larger external screen with additional software. The term personal computer is meant to include but is not limited to desktop computers, laptop computers, tablets, and the like. The spirometer 30 may be coupled to an external display device through one or more coupling devices, such as a USB cable, a serial cable, a headphone cable, a specially configured cord, and combinations therein. Accordingly, embodiments of the spirometer 30 may comprise any of a USB cable, a serial cable, a headphone cable, and combinations thereof. The spirometer 30 may also be configured to be coupled to an external display device by a wireless connection. For example, the spirometer 30 may be configured to be coupled to an external display device using Bluetooth technology, SMS messages, WIFI technology, GSM technology, infrared transmission, or fiber optics. Accordingly, embodiments of the spirometer 30 may comprise a Bluetooth transmitter. In at least one embodiment, the display device may be integral with the spirometer 30. For example, the spirometer 30 may comprise an LCD display, an LED display, an organic LED display, a raised touch pad, or combinations thereof. The mobile phone and the portable computer are connected to the Internet by an Internet gateway device (e.g., a modem). The mobile phone and the portable computer may also communicate with the Internet gateway device using WIFI protocols, Bluetooth protocols, and the like. By way of a non-limiting example, the data may be transmitted by the device 30 via a radio link (e.g., the radio link) to the desktop computer, the cellular telephone, the portable computer, and the like. By way of another non-limiting example, the information may be transmitted by the device directly to the Internet gateway device.

In some embodiments, the mobile computing device may contribute related but not necessarily equivalent information to the spirometer 30 and additionally transmit or analyze this information alongside lung function results. By way of a non-limiting example, this information may include geopositional location, local weather forecasts, altitude, temperature, humidity, or any other information that is passively or actively collected by the device or associated devices that may or may not be directly considered as health information. By way of another non-limiting example, such external information may be used collectively with transmitted patient lung function results to train one or more learning algorithms to make a plurality of predictions on how such information may be related to changes in lung function. With reference to this latter embodiment, the training, testing, and deployment of such learning algorithms may be done across one or multiple processor units, possibly including the mobile computing device, a remote server, a personal computer, or a combination thereof.

In some embodiments, a personal computer, a connected server, or a smartphone may comprise an application that is used to perform any or all of the following: track or monitor the output data over a period of time or a number of uses, analyze the output data to provide additional lung performance information, display the output data graphically in a variety of formats, interface with other devices for offsite review or interpretation, and combinations thereof. By way of a non-limiting example, all or parts of this physiological information may be shared through a remote server securely in a regulatory compliant manner (e.g. HIPAA in the USA) with health coaches, physicians and other healthcare professionals, family members, electronic medical records, patient registries, clinical trial centers, and/or any other individual, organization, or corporate entity with appropriate permissions. Such information in raw and analyzed form could be used to prevent unnecessary visits to the office of a health care professional or hospital by identifying a negative change in the respiratory function of patients and may further permit remote teleconferencing with at-risk patients.

Networking of patient airflow testing, and even medication administration, provide numerous advantages over conventional clinical practice. Adherence to a treatment plan is likely to improve if it is measured, monitored, and adapted. In some embodiments, the spirometer 30 and associated software may be used to gather lung function data pre- and post-administration of a particular therapy, which may or may not be a small molecule drug, biologic, or the like, to show proper compliance (e.g. 3 times per day) and/or usage (e.g. following a particular protocol to administer the medication). The act of monitoring of human behavior can change it. Providing real-time data to a network may improve compliance. Compliance may be directly monitored by the recognition of insufficient usage of a maintenance medication, as revealed by poor improvement in lung function, or may be inferred if spirometry is prescribed alongside a medication and the spirometry tests themselves are found to be missing or incomplete. The system in some embodiments can function as a medication reminder for those patients with a consistent dosage treatment plan who miss an application or overuse a medicine.

By automatically providing trended data to the healthcare provider, he or she can review the effectiveness of the treatment plan and make adjustments as needed. In many cases, the patient data review and adjustment of treatment plan may be accomplished without a visit to a practitioner, which may reduce medical costs and improve healthcare outcomes. More generally, the system embodied in the device enables the healthcare provider to better monitor and manage their patients with chronic respiratory disease on a continual basis. In addition to the supervisory function, the system can also function as a means of providing information and education to the patient, sending messages directly to the patient's computing device or a patient support network to educate and generally inform.

The healthcare provider may access the data to review the airflow measurements to detect potential problems or recommend treatment or changes in treatment. Likewise, the absence of event tracking information might inform a user or caregiver of a missed scheduled medication administration or measurement event, or even a prolonged loss of contact that may indicate a device failure. In some embodiments, this could trigger a message to the appropriate individuals in charge of a patient's care.

Messages sent to the healthcare system and/or the patient may include SMS cellular telephone messages, recorded voice messages (e.g., including educational information), alerts, alarms, and the like. Thus, means are provided for assessing changes in the medicine administration and the lung function of a patient and more particularly the onset of a respiratory disease symptoms and concomitant exacerbations. The assessment may be conducted remotely by the healthcare provider or within a healthcare provider's office.

The healthcare provider may be connected via the Internet and messages to be reviewed by a caregiver may be transmitted and displayed on a secure website. In one embodiment, the computing device is connected to the Internet via a wired communication link and in another embodiment this link may be wireless. The computing device may connect to the web server over the Internet and may display the website using a conventional or specialized web browser application.

The new spirometer and concomitant software described has many advantages, including in mobile tracking of lung function or the improvement of lung performance. It is contemplated that embodiments of the spirometer may find particular use by non-patients, including but not limited to athletes, runners, bikers, musicians, singers, smokers, ex-smokers, video gamers, children, and the like, to evaluate, track, train, or improve lung function. It is especially contemplated that embodiments of the spirometer are used in connection with an "app" or a computer program to track improvements in lung performance over time. In one non-limiting embodiment, the "app" or program may provide user incentives to use the device consistently, inclusive of virtual points that may or may not be redeemable for real life prizes, lottery entries for cash-value rewards, direct or indirect financial compensation, virtual or real (i.e. printable) achievements and certificates, virtual or real (i.e. printable) contracts between the user and themselves or any other real or virtual individual, or any combination thereof. In another non-limiting embodiment, the "app" or program could securely and remotely link the user with a health coach, physician, or any other healthcare professional to give personalized verbal encouragement and training incentives via teleconferencing. In another non-limiting embodiment, these actions may be mediated directly or indirectly by a virtual avatar that learns the user's behavior and personality via a plurality of learning algorithms and then gives the user personalized feedback or encouragement on their health. In some embodiments, the "app" or computer program could use animations (e.g. blowing a dandelion using digital exhalation input from the described spirometer), games (e.g. "throwing" darts at a dartboard using digital exhalation input and positional and angular information from the described spirometer), and the like to incentivize use of the spirometer to evaluate, track, train, or improve lung performance. Thus, the spirometer comprises a key component in an overall comprehensive management platform, which provides the regular use of a lung function test in order to provide objective measures of a user's lung function.

Some aspects of the present description describe embodiments of the present invention with regard to treating asthma and COPD conditions, but it will be appreciated by a person of ordinary skill in the art that the present invention is applicable to other airway disorders as well. In some embodiments, the device may be used by individuals not afflicted by any particular respiratory disorder for interest in evaluating, tracking, training, or improving lung performance.

Figure 16A:
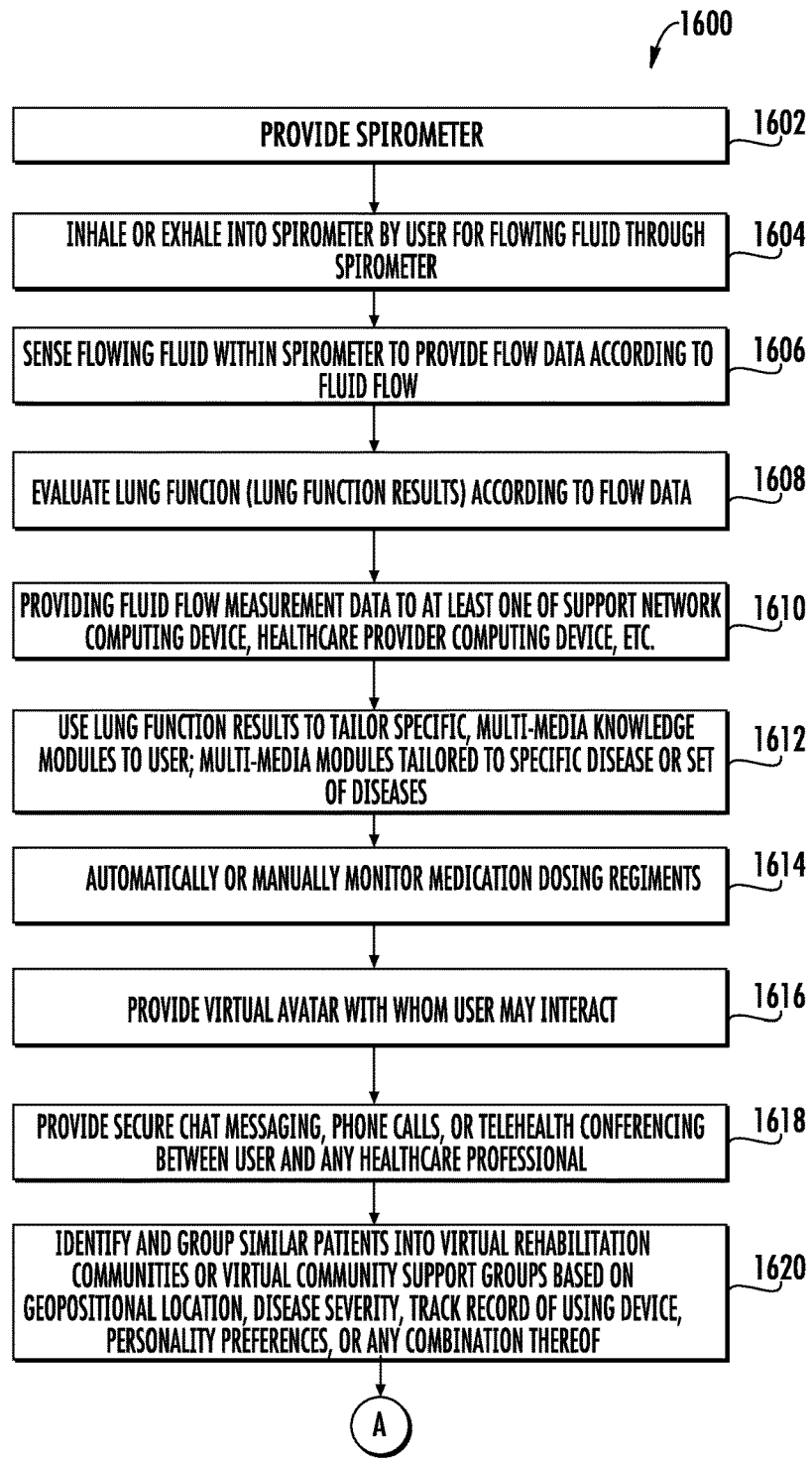
FIGS. 16A and 16B are a flow chart of an example of method 1600 for delivering the contents of a pulmonary rehabilitation program to a user in accordance with an embodiment of the present invention.
Figure 16B:
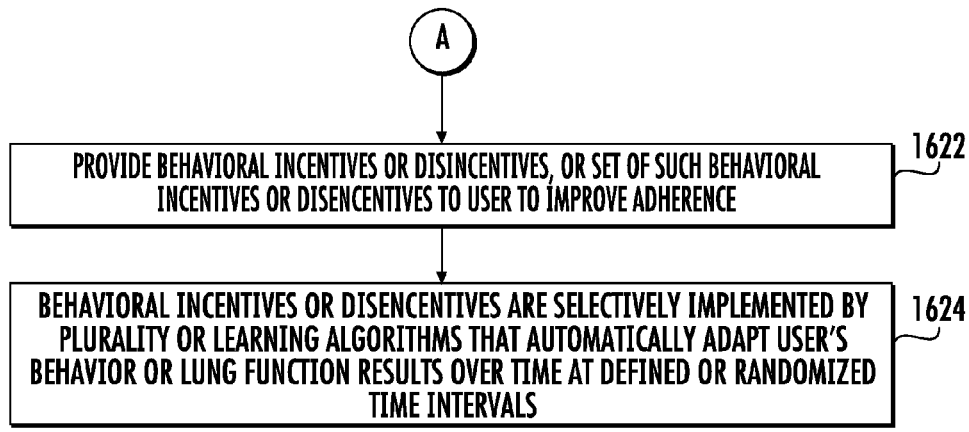

Based on the description above FIGS. 16A and 16B are a flow chart of an example of method 1600 for delivering the contents of a pulmonary rehabilitation program in accordance with an embodiment of the present invention. In block 1602, a spirometer is provided for sensing fluid flow from the individual or user breathing through the spirometer. The spirometer is similar to any of the embodiments described herein.

In block 1604, the user breaths into the spirometer by exhaling or inhaling for flowing fluid through the spirometer from the first end to exit the second end. In block 1606, flowing fluid is sensed within the spirometer to provide flow data according to the fluid flow. In block 1608, lung function is evaluated according to the flow data as described herein. In block 1610, the fluid flow measurement data is provided to at least one of a support network computing device and a healthcare provider computing device. The support network computing device or the healthcare provider computing device employs any variety or set of learning algorithms to automatically diagnose an individual's respiratory condition based on the flow data or any other user-specific health information in combination with the flow data.

In block 1612, the lung function results are used to tailor specific, multi-media knowledge modules to the user or individual. The multi-media knowledge modules are tailored to a specific disease or set of diseases. In block 1614, medication dosing regimens are automatically or manually monitored.

In block 1616, a virtual avatar may be provided with whom the individual or user interacts. In block 1618, secure chat messaging, phone calls, or telehealth conferencing is provided between the individual and any healthcare professional.

In block 1620, similar patients are identified and grouped into virtual rehabilitation communities or virtual community support groups based on geopositional location, disease severity, track record of using the device, personality preferences, or any combination thereof. The virtual community support groups are able to communicate via secure group chat messaging, phone calls, or telehealth conferencing. The virtual community support groups also have synchronized behavioral incentives, medication reminders, and task checklists. The virtual community support groups are also able to congregationally communicate with a plurality of doctors, nurses, therapists, health coaches, or any combination thereof in real-time via secure group chat messaging, phone calls, or telehealth conferencing.

In block 1622, a behavioral incentive or disincentive, or a set of such behavioral incentives or disincentives, are provided to the individual or user to improve adherence to the rehabilitation program. The behavioral incentives or disincentives may include but is not necessarily limited to virtual, real, or transferable (i.e. virtual to real) rewards, achievements, coupons, currencies, cryptocurrencies, non-financial compensation, or any combination thereof at defined or randomized time intervals. The behavioral incentives or disincentives are selectively implemented by a plurality of learning algorithms that automatically adapt to the user's behavior or lung function results over time at defined or randomized time intervals. The behavioral incentives or disincentives may include animations, games, augmented reality, or any combination thereof whose functions are tied directly or indirectly to lung function readings.

Figure 17:
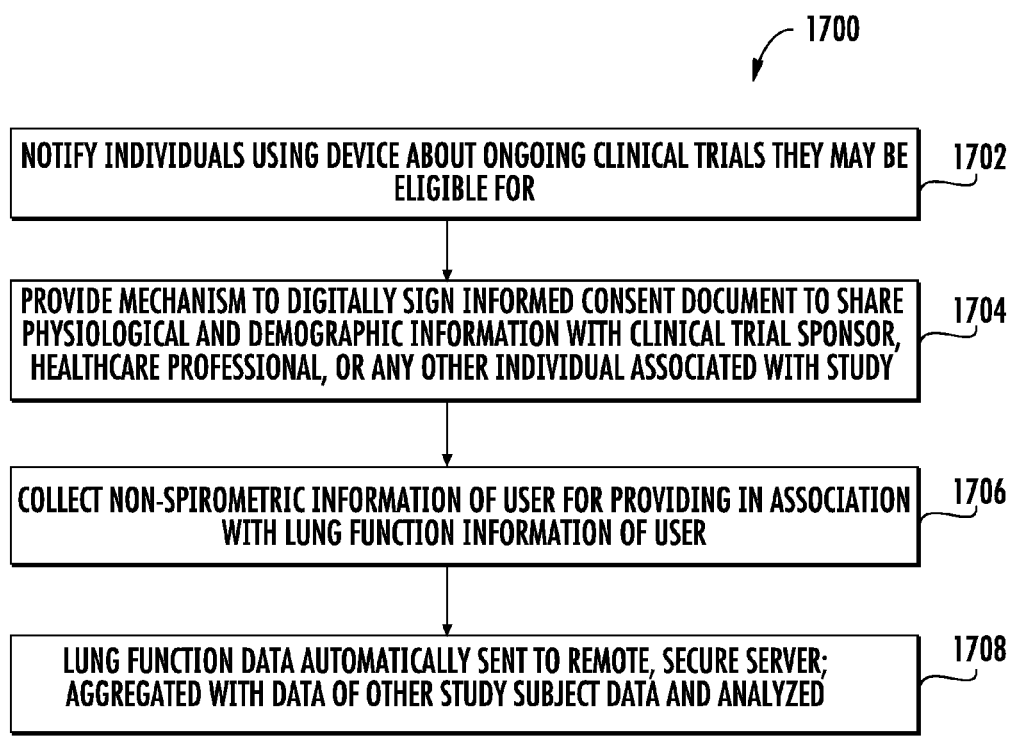
FIG. 17 is a flow chart of an example of a method 1700 for remotely engaging individuals in clinical trials or research studies in accordance with an embodiment of the present invention.

FIG. 17 is a flow chart of an example of a method 1700 for remotely engaging individuals in clinical trials or research studies in accordance with an embodiment of the present invention. In block 1702, users who are already using the device or spirometer are notified through the software associated with the device about ongoing clinical trials that they may be eligible for.

In block 1704, users can digitally sign an informed consent document to share their physiological and demographic information with a clinical trial sponsor, healthcare professional, or any other privileged individual associated with the study.

In block 1706, a plurality of non-spirometric information is collected and shared by the user alongside his or her personal lung function information. The non-spirometric information may be collected by means other than the spirometer. A behavioral incentive or disincentive, or a set of such behavioral incentives or disincentives, may be provided to the study subject to improve adherence to study protocol.

In block 1708, lung function data is automatically sent to a remote, secure server. The lung function data is aggregated with other study subject data or with data from other participants in the study and analyzed.

In accordance with different embodiments, users are compensated before the study, during the study, after the study, or any combination thereof. The users are compensated based on personal or group adherence to a specific clinical trial protocol. In accordance with embodiments, the study subjects are compensated with virtual, real, or transferable (i.e. virtual to real) rewards, achievements, coupons, currencies, cryptocurrencies, non-financial compensation, or any combination thereof at defined or randomized time intervals.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of embodiments of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although the present invention has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages, particularly in light of the foregoing teachings. Accordingly, we intend to cover all such modifications, omission, additions and equivalents as may be included within the spirit and scope of the invention as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. A spirometer for sensing fluid flow from an individual breathing through the spirometer, the spirometer comprising:
   a tubular housing having an open first end and an open second end, the housing defining
      a first fluid flow pathway extending between the first end and the second end,
      a first opening along the first fluid flow pathway and through which fluid flow enters, and
      a second opening longitudinally spaced along the first fluid flow pathway from the first opening and through which fluid flow enters;
   a flow chamber having a central longitudinal axis and defining a second fluid flow pathway, the flow chamber disposed within the housing between the first opening and the second opening, the flow chamber including an elongated resistive element along the central longitudinal axis of the flow chamber, and at least elongated tubular element disposed between the resistive element and the inner surface of the flow for defining a plurality of annular flow passages through the flow chamber between the resistive element and the inner surface of the flow chamber, wherein the flow chamber conditions fluid flow for accurate sensing of the flow over a range of fluid flow through the housing; and
   a pressure sensor disposed within the housing, the pressure sensor in fluid communication with the first opening and the second opening for sensing a pressure differential between the first opening and the second opening and producing an electric signal in response to fluid flow through the housing, wherein the electric signal has a magnitude that corresponds with the rate of fluid flow through the housing and a sign that corresponds with the directionality of fluid flow through the housing.

2. The spirometer as recited in claim 1, wherein fluid through the flow chamber is substantially parallel to the longitudinal axis of the flow chamber.

3. The spirometer as recited in claim 1, wherein the flow chamber and the pressure sensor have no moving parts.

4. The spirometer as recited in claim 1, wherein the flow chamber has a cylindrical cross-section.

5. The spirometer as recited in claim 1, wherein the elongated tubular element is removable from the rest of the device.

6. The spirometer as recited in claim 1, wherein the flow chamber is configured to laminarize the fluid flow.

7. The spirometer as recited in claim 1, wherein the pressure sensor is a transducer.

8. The spirometer as recited in claim 1, wherein the pressure sensor is a self-calibrating transducer.

9. The spirometer as recited in claim 1, wherein the pressure sensor is configured to be connected to a display device or mobile computing device.

10. The spirometer as recited in claim 9, wherein the spirometer is configured to be connected to the display device or mobile computing device by a physical connection.

11. The spirometer of claim 9, wherein the spirometer further comprises a radio frequency transmitter (RF) configured to be connected to a display device or mobile computing device by a wireless connection.

12. The spirometer as recited in claim 9, wherein the display device or mobile computing device is a smartphone.

13. The spirometer as recited in claim 9, wherein the display device or mobile computing device is a personal computer.

14. The spirometer as recited in claim 9, wherein the display device or mobile computing device is a remote server.

15. The spirometer as recited in claim 1, further comprising a mouth piece configured to be attached to the first end of the housing, the mouth piece having an opening through the mouth piece for transmitting human breath.

16. The spirometer as recited in claim 15, wherein the mouth piece is releasably attached to the housing for changing the mouth piece for use with different patients.

17. A lung function testing system for an individual, the lung function testing system comprising:
    a spirometer for sensing fluid flow from the individual breathing through the spirometer, the spirometer comprising
        a tubular housing having an open first end and an open second end, the housing defining a first fluid flow pathway extending between the first end and the second end, a first opening along the first fluid flow pathway and through which fluid flow enters, and a second opening longitudinally spaced along the first fluid flow pathway from the first opening and through which fluid flow enters,
        a flow chamber having a central longitudinal axis and defining a second fluid flow pathway, the flow chamber disposed within the housing between the first opening and the second opening, the flow chamber including an elongated resistive element along the central longitudinal axis of the flow chamber, and at least elongated tubular element disposed between the resistive element and the inner surface of the flow chamber for defining a plurality of annular flow passages through the flow chamber between the resistive element and the inner surface of the flow chamber, wherein the flow chamber conditions the fluid flow for accurate sensing of the flow over a range of fluid flow through the housing, and
        a pressure sensor disposed within the housing, the pressure sensor in fluid communication with the first opening and the second opening for sensing a pressure differential between the first opening and the second opening and producing an electric signal in response to fluid flow through the housing, wherein the electric signal has a magnitude that corresponds with the rate of fluid flow through the housing and a sign that corresponds with the directionality of fluid flow through the housing; and
    a microprocessor coupled to the pressure sensor for data acquisition and processing the electrical signal to evaluate lung function according to the fluid flow rate through the housing.

18. The lung function testing system as recited in claim 17, further comprising a transmitter, and an external device comprising a display device or mobile computing device for monitoring the individual, wherein the spirometer and the external device are each connected by at least one network, the spirometer being operable to collect at least one fluid flow measurement of the individual and transmit the at least one fluid flow measurement to the at least one network.

19. A method of evaluating respiratory fluid flow of an individual, the respiratory fluid flow evaluation method comprising the steps of:
    providing a spirometer for sensing fluid flow from the individual breathing through the spirometer, the spirometer comprising
        a tubular housing having an open first end and an open second end, the housing defining a first fluid flow pathway extending between the first end and the second end, a first opening along the first fluid flow pathway and through which fluid flow enters, and a second opening longitudinally spaced along the first fluid flow pathway from the first opening and through which fluid flow enters,
        a flow chamber having a central longitudinal axis and defining a second fluid flow pathway, the flow chamber disposed within the housing between the first opening and the second opening, the flow chamber including an elongated resistive element along the central longitudinal axis of the flow chamber, and at least elongated tubular element disposed between the resistive element and the inner surface of the flow chamber for defining a plurality of annular flow passages through the flow chamber between the resistive element and the inner surface of the flow chamber, wherein the flow chamber conditions the fluid flow for accurate sensing of the flow over a range of fluid flow through the housing, and
        a pressure sensor disposed within the housing, the pressure sensor in fluid communication with the first opening and the second opening for sensing a pressure differential between the first opening and the second opening and producing an electric signal in response to fluid flow through the housing, wherein the electric signal has a magnitude that corresponds with the rate of fluid flow through the housing and a sign that corresponds with the directionality of fluid flow through the housing;
    breathing into the spirometer by exhaling or inhaling for flowing fluid through the spirometer from the first end to exit the second end;
    sensing flowing fluid within the spirometer to provide flow data according to the fluid flow; and
    evaluating lung function according to the flow data.

20. The respiratory fluid flow evaluation method as recited in claim 19, further comprising the step of providing fluid flow measurement data to at least one of a support network computing device and a healthcare provider computing device.

21. The respiratory fluid flow evaluation method as recited in claim 19, further comprising the step of providing fluid flow measurement data to a healthcare provider computing device.

22. The respiratory fluid flow evaluation method as recited in claim 19, wherein software linked to the support network computing device or the healthcare provider computing device employs any variety or set of learning algorithms to automatically diagnose an individual's respiratory condition based on the flow data or any other user-specific health information in combination with the flow data.

* * * * *

UNITED STATES PATENT AND TRADEMARK OFFICE
CERTIFICATE OF CORRECTION

PATENT NO. : 10,098,570 B2
APPLICATION NO. : 15/696780
DATED : October 16, 2018
INVENTOR(S) : Gregory Poore et al.

Page 1 of 1

It is certified that error appears in the above-identified patent and that said Letters Patent is hereby corrected as shown below:

On the Title Page

Item (72), should read as follows:
Gregory Poore, La Jolla, CA (US);
Daniel Chander, Villa Martia (SG);
Jinsu Kim, Gainesville, FL (US);
Melody Xuan Lim, Chicago, IL (US)

Signed and Sealed this
First Day of January, 2019

Andrei Iancu
*Director of the United States Patent and Trademark Office*